United States Patent [19]

Anderson et al.

[11] Patent Number: 5,298,407
[45] Date of Patent: Mar. 29, 1994

[54] DNA ENCODING A PROTEIN ACTIVE IN LYMPHOCYTE-MEDIATED CYTOTOXICITY

[75] Inventors: Paul J. Anderson, Watertown; Michel Streuli, Somerville; Stuart F. Schlossman, Newton Centre, all of Mass.

[73] Assignee: Dana-Farber Cancer Institute, Inc., Boston, Mass.

[21] Appl. No.: 726,607

[22] Filed: Jul. 10, 1991

Related U.S. Application Data

[63] Continuation-in-part of Ser. No. 460,678, Jan. 5, 1990, abandoned.

[51] Int. Cl.$^5$ .................. C12Q 1/68; C12N 15/00; C07K 13/00
[52] U.S. Cl. ........................ 435/69.1; 435/6; 435/320.1; 435/240.2; 435/240.27; 530/350; 530/388.73; 530/387.9; 530/388.75; 536/23.5; 536/24.31
[58] Field of Search .............. 435/6, 69.1; 530/350; 536/27; 424/520

[56] References Cited

U.S. PATENT DOCUMENTS 4,125,648  5/1990  Hansen et al. .................. 530/402

FOREIGN PATENT DOCUMENTS 0314500   5/1989   European Pat. Off. .
WO87/03910 7/1987  PCT Int'l Appl. .
WO90/15822 12/1990 PCT Int'l Appl. .

OTHER PUBLICATIONS

Anderson et al., J. of Immunology 144:574-582 (1990).
Meuer et al., Proc. Natl. Acad. Sci. USA 79:4395-4399 (1982).
Reinherz et al., Immunological Rev. 74:83-112 (1983).
Podack et al., J. Exp. Med. 160:695-710 (1984).
Podack et al., Proc. Natl. Acad. Sci. USA 82:8629-8633 (1985).
Shinkai et al., Nature 334:525-527 (1988).
Lowrey et al., Proc. Natl. Acad. Sci. USA 86:247-251 (1989).
Pasternak et al., Nature 314:743-745 (1985).
Pasternack et al., Nature 322:740-743 (1986).
Young et al., Cell 47:183-194 (1986).
Schmidt et al., J. of Immunology 142:991-1002 (1988).
Kamada et al., J. of Immunology, 142:609-615 (1989).
Takayama et al., J. of Immunology 138:566-569 (1987).
Schmidt et al., Nature 318:289-291 (1985).
Kriegler et al., Cell 53:45-53 (1988).
Yamamoto et al., J. of Immunology 137:1878-1884 (1986).
Schmid et al., Proc. Natl. Acad. Sci. USA 83:1881-1885 (1986).
Fiskum et al., Proc. Natl. Acad. Sci. USA 77:3430-3434 (1980).
Anderson et al., J. of Immunology 143:1899-1904 (1989).
Willingham et al., Proc. Natl. Acad. Sci. USA 75:4359-4363 (1978).

Primary Examiner—Robert J. Hill, Jr.
Assistant Examiner—K. Cochrane Carlson
Attorney, Agent, or Firm—Fish & Richardson

[57] ABSTRACT

An isolated DNA that includes a sequence encoding a polypeptide with which the monoclonal antibody TIA-1 produced by the hybridoma designated ATCC#HB10319 is immunologically reactive; a vector or a cell containing such a DNA; and a method of using such a DNA to identify cytolytic lymphocytes.

15 Claims, 18 Drawing Sheets

```
-56                                                                              GA  GGT  AGT
-48      GAA  GGG  CAG  GGA  GCT  GGA  CCT  GGA  GGC  GCC  GCC  GCG  ACA  GCA  GCA  GCC

+1       ATG  GAG  GAC  GAG  ATG  CCC  AAG  ACT  CTA  TAC  GTC  GGT  AAC  CTT  TCC  AGA
  +1      M    E    D    E    M    P    K    T    L    Y    V    G    N    L    S    R

+49      GAT  GTG  ACA  GAA  GCT  CTA  ATT  CTG  CAA  CTC  TTT  AGC  CAG  ATT  GGA  CCT
 +17      D    V    T    E    A    L    I    L    Q    L    F    S    Q    I    G    P

+97      TGT  AAA  AAC  TGC  AAA  ATG  ATT  ATG  GAT  ACA  GCT  GGA  AAT  GAT  CCC  TAT
 +33      C    K    N    C    K    M    I    M    D    T    A    G    N    D    P    Y

+145     TGT  TTT  GTG  GAG  TTT  CAT  GAG  CAT  CGT  CAT  GCA  GCT  GCA  GCA  TTA  GCT
 +49      C    F    V    E    F    H    E    H    R    H    A    A    A    A    L    A

+193     GCT  ATG  AAT  GGA  CGG  AAG  ATA  ATG  GGT  AAG  GAA  GTC  AAA  GTG  AAT  TGG
 +65      A    M    N    G    R    K    I    M    G    K    E    V    K    V    N    W

+241     GCA  ACA  ACC  CCT  AGC  AGT  CAA  AAG  AAA  GAT  ACA  AGC  AAT  CAT  TTC  CAT
 +81      A    T    T    P    S    S    Q    K    K    D    T    S    N    H    F    H

+289     GTC  TTT  GTT  GGT  GAT  CTC  AGC  CCA  CAA  ATT  ACA  ACT  GAA  GAT  ATA  AAA
 +97      V    F    V    G    D    L    S    P    Q    I    T    T    E    D    I    K

+337     GCT  GCT  TTT  GCA  CCA  TTT  GGA  AGA  ATA  TCA  GAT  GCC  CGA  GTG  GTA  AAA
+113      A    A    F    A    P    F    G    R    I    S    D    A    R    V    V    K

+385     GAC  ATG  GCA  ACA  GGA  AAG  TCT  AAG  GGA  TAT  GGC  TTT  GTC  TCC  TTT  TTC
+129      D    M    A    T    G    K    S    K    G    Y    G    F    V    S    F    F

+433     AAC  AAA  TGG  GAT  GCT  GAA  AAC  GCC  ATT  CAA  CAG  ATG  GGT  GGC  CAG  TGG
+145      N    K    W    D    A    E    N    A    I    Q    Q    M    G    G    Q    W

+481     CTT  GGT  GGA  AGA  CAA  ATC  AGA  ACT  AAC  TGG  GCA  ACC  CGA  AAG  CCT  CCC
+161      L    G    G    R    Q    I    R    T    N    W    A    T    R    K    P    P

+529     GCT  CCA  AAG  AGT  ACA  TAT  GAG  TCA  AAT  ACC  AAA  CAG  CTA  TCA  TAT  GAT
+177      A    P    K    S    T    Y    E    S    N    T    K    Q    L    S    Y    D

+577     GAG  GTT  GTA  AAT  CAG  TCT  AGT  CCA  AGC  AAC  TGT  ACT  GTA  TAC  TGT  GGA
+193      E    V    V    N    Q    S    S    P    S    N    C    T    V    Y    C    G

+625     GGT  GTT  ACT  TCT  GGG  CTA  ACA  GAA  CAA  CTA  ATG  CGT  CAG  ACT  TTT  TCA
+209      G    V    T    S    G    L    T    E    Q    L    M    R    Q    T    F    S

+673     CCA  TTT  GGA  CAA  ATA  ATG  GAA  ATT  CGA  GTC  TTT  CCA  GAT  AAA  GGA  TAT
+225      P    F    G    Q    I    M    E    I    R    V    F    P    D    K    G    Y

+721     TCA  TTT  GTT  CGG  TTC  AAT  TCC  CAT  GAA  AGT  GCA  GCA  CAT  GCA  ATT  GTT
+241      S    F    V    R    F    N    S    H    E    S    A    A    H    A    I    V

+769     TCT  GTT  AAT  GGT  ACT  ACC  ATT  GAA  GGT  CAT  GTT  GTG  AAA  TGC  TAT  TGG
+257      S    V    N    G    T    T    I    E    G    H    V    V    K    C    Y    W
```

FIG. 1a

```
+817  GGC AAA GAA ACT CTT GAT ATG ATA AAT CCC GTG CAA CAG CAG AAT CAA
+273   G   K   E   T   L   D   M   I   N   P   V   Q   Q   Q   N   Q

+865  ATT GGA TAT CCC CAA CCT TAT GGC CAG TGG GGC CAG TGG TAT GGA AAT
+289   I   G   Y   P   Q   P   Y   G   Q   W   G   Q   W   Y   G   N

+913  GCA CAA CAA ATT GGC CAG TAT ATG CCT AAT GGT TGG CAA GTT CCT GCA
+305   A   Q   Q   I   G   Q   Y   M   P   N   G   W   Q   V   P   A

+961  TAT GGA ATG TAT GGC CAG GCA TGG AAC CAG CAA GGA TTT AAT CAG ACA
+321   Y   G   M   Y   G   Q   A   W   N   Q   Q   G   F   N   Q   T

+1009 CAG TCT TCT GCA CCA TGG ATG GGA CCA AAT TAT GGA GTG CAA CCG CCT
+337   Q   S   S   A   P   W   M   G   P   N   Y   G   V   Q   P   P

+1057 CAA GGG CAA AAT GGC AGC ATG TTG CCC AAT CAG CCT TCT GGG TAT CGA
+353   Q   G   Q   N   G   S   M   L   P   N   Q   P   S   G   Y   R

+1105 GTG GCA GGG TAT GAA ACC CAG TGA ATA AGG ACT CCA GAA TCT AAA GCC
+369   V   A   G   Y   E   T   Q

+1153 AGT GGC TTG AGG CTA CAG GGA GTG TAG TAA AGC CGT TGT TTA CTT AAA
+1201 GAT TTA TCA AAT CAG TCA GTG CAA ATG TCA GAT ACA ATG TAT TTA TTT
+1249 AAA AGA TTC ATT TTT AAT CAT GAA ATT ACT TAT CAT CCA CAT TGT TTT
+1297 AAA AAG AAA CAA GAT GCT GGA TGT CTG CCA ATT TTT GCC TTC ATT ACC
+1345 TTT TTT GAT AAA GTT TCT CAG ATC CTT GTT TCA AAC ACA AAT GCA GGG
+1393 ATT GCT GCC ACT TTT TAA CTA TTA AGA GGC AGA AAA TTG CAC AAT ATT
+1441 GAA CTT TTT TCC ACT GAA GTA GTG TGC AGT TCT AGT TTG CAT TCC TGA
+1489 TAT GAT TTA AAA CAT GTA ATA TAA AGA TGT TAA AAA AAA AAA CCA AAA
+1537 CTG TGC AGA GTC TAG AAG TTG TTT GTC ATC TTC AGC TTG TGC ACA ATT
+1585 CTG TTT TAG GTT AAA AAA AGG CAT TGT TTG AGC TGT CCC ATC TCC ACT
+1633 GTT ATC CCT TTG GGT TTT TTA ATA AAT TAT TAG TTA CAT CAT TTT
+1681 TGT ATC TAC ATC TTT TTT CAC AAA TTT GTC TTG CCT TAT TAA AGT TCT
+1729 GTA AAA TAT ACT TAA ATG GAA AAA ATG ATG TTC ATT TAG ATT GAA AAC
+1777 TTT TCT CAG ATG GAT TGA TAA TTG CAT TCA TCT TGT GTT TTA TAT GAG
+1825 AAG GTG CCT CAA GAA TTT CCT GTT GGA TTT GTT TAA AAG GAT TTT TAT
+1873 CTT TCG TGA TAA ACT TTG CTG TGT ACC AGG AAC TAT AAA AAC AAA AAC
+1921 TTG TTA CTA AAG AAA ATA TCT GAA ATG TGA TAA GTT CTT ATG CCA TGT
+1969 TAA TTT CAT GTG TCA ACT TCA ACA TTT ACA TGT ATT ATT TCA TTA TGT
+2017 AAA ATG TTT TAG CAA TTT AAT ATT TTG CAC AGT TAG CAA ACT TTG TAT
+2065 GTC ATT TCC TTC AAG GCA TCA TGC AGA GTT GAC ATG AGA TTT ATA AGG
+2113 TTT TAA GTT GTT TGC ATG TGA AAA TCA AAT ACA TAC TTT GGT AGT CTT
+2161 TGA AAA AAA AAA
```

FIG. 1b

```
TACCAAACAG CTATCATATG ATGAGGTTGT AAATCAGTCT AGTCCAAGCA ACTGTACTGT    60

ATACTGTGGA GGTGTTACTT CTGGGCTAAC AGAACAACTA ATGCGTCAGA CTTTTTCACC   120

ATTTGGACAA ATA ATG GAA ATT CGA GTC TTT CCA GAT AAA GGA TAT         166
           Met Glu Ile Arg Val Gly Pro Asp Lys Gly Tyr
            1           5                    10
TCA TTT GTT CGG TTC AAT TCC CAT GAA AGT GCA GCA CAT GCA ATT GTT    214
Ser Phe Val Arg Phe Asn Ser His Glu Ser Ala Ala His Ala Ile Val
            15                  20                  25
TCT GTT AAT GGT ACT ACC ATT GAA GGT CAT GTT GTG AAA TGC TAT TGG    262
Ser Val Asn Gly Thr Thr Ile Glu Gly His Val Val Lys Cys Tyr Trp
        30                  35                  40
GGC AAA GAA ACT CTT GAT ATG ATA AAT CCC GTG CAA CAG CAG AAT CAA    310
Gly Lys Glu Thr Leu Asp Met Ile Asn Pro Val Gln Gln Gln Asn Gln
        45                  50                  55
ATT GGA TAT CCC CAA CCT TAT GGC CAG TGG GGC CAG TGG TAT GGA AAT    358
Ile Gly Tyr Pro Gln Pro Tyr Gly Gln Trp Gly Gln Trp Tyr Gly Asn
60                  65                  70                  75
GCA CAA CAA ATT GGC CAG TAT ATG CCT AAT GGT TGG CAA GTT CCT GCA    406
Ala Gln Gln Ile Gly Gln Tyr Met Pro Asn Gly Trp Gln Val Pro Ala
            80                  85                  90
TAT GGA ATG TAT GGC CAG GCA TGG AAC CAG CAA GGA TTT AAT CAG ACA    454
Tyr Gly Met Tyr Gly Gln Ala Trp Asn Gln Gln Gly Phe Asn Gln Thr
            95                  100                 105
CAG TCT TCT GCA CCA TGG ATG GGA CCA AAT TAT GGA GTG CAA CCG CCT    502
Gln Ser Ser Ala Pro Trp Met Gly Pro Asn Tyr Gly Val Gln Pro Pro
            110                 115                 120
CAA GGG CAA AAT GGC AGC ATG TTG CCC AAT CAG CCT TCT GGG TAT CGA    550
Gln Gly Gln Asn Gly Ser Met Leu Pro Asn Gln Pro Ser Gly Tyr Arg
        125                 130                 135
GTG GCA GGG TAT GAA ACC CAG                                        571
Val Ala Gly Tyr Glu Thr Gln
140                 145
                                    TGAATAAGGA CTCCAGAATC TAAAGCC   598
AGTGGCTTGA GGCTACAGGG AGTGTAGTAA AGCCGTTGTT TACTTAAAGA TTTATCAAAT  658
CAGTCAGTGC AAATGTCAGA TACAATGTAT TTATTTAAAA GATTCATTTT TAATCATGAA  718
ATTACTTATC ATCCACATTG TTTTAAAAAG AAACAAGATG CTGGATGTCT GCCAATTTTT  778
GCCTTCATTA CCTTTTTTGA TAAAGTTTCT CAGATCCTTG TTTCAAACAC AAATGCAGGG  838
ATTGCTGCCA CTTTTTAACT ATTAAGAGGC AGAAAATTGC ACAATATTGA ACTTTTTTCC  898
ACTGAAGTAG TGTGCAGTTC TAGTTTGCAT TCCTGATATG ATTTAAAACA TGTAATATAA  958
AGATGTTAAA AAAAAAAACC AAAACTGTGC AGAGTCTAGA AGTTGTTTGT CATCTTCAGC 1018
TTGTGCACAA TTCTGTTTTA GGTTAAAAAA AGGCATTGTT TGAGCTGTCC CATCTCCACT 1078
GTTATCCCTT TGGGTTTTTT AATATAAATT ATTAGTTTAC ATCATTTTTG TATCTACATC 1138
TTTTTTCACA AATTTGTCTT GCCTTATTAA AGTTCTGTAA AATATACTTA AATGGAAAAA 1198
ATGATGTTCA TTTAGATTGA AAACTTTTCT CAGATGGATT GATAATTGCA TTCATCTTGT 1258
GTTTTATATG AGAAGGTGCC TCAAGAATTT CCTGTTGGAT TTGTTTAAAA GGATTTTTAT 1318
CTTTCGTGAT AAACTTTGCT GTGTACCAGG AACTATAAAA ACAAAAACTT GTTACTAAAG 1378
AAAATATCTG AAATGTGATA AGTTCTTATG CCATGTTAAT TTCATGTGTC AACTTCAACA 1438
TTTACATGTA TTATTTCATT ATGTAAAATG TTTTAGCAAT TTAATATTTT GCACAGTTAG 1498
CAAACTTTGT ATGTCATTTC CTTCAAGGCA TCATGCAGAG TTGACATGAG ATTTATAAGG 1558
TTTTAAGTTG TTTGCATGTG AAAATCAAAT ACATACTTTG GTAGTCTTTG AAAAAAAAAA 1618
```

FIG. 2

STRUCTURAL MOTIFS EXPRESSED BY TIA-1 cDNAs

EXPRESSION OF LYSOSOMAL MEMBRANE MOTIF AT THE CARBOXY TERMINUS OF TIA-1

DNA ENCODING A PROTEIN ACTIVE IN LYMPHOCYTE-MEDIATED CYTOTOXICITY

This application is a continuation-in-part of pending application Ser. No. 460,678, filed on Jan. 5, 1990, now abandoned.

The invention was made in the course of an award or grant from the Arthritis Foundation and the National Institutes of Health, and the United States government, therefore, has certain rights in this invention.

This invention relates to recombinant nucleic acid encoding animal proteins, and specifically to nucleic acid encoding proteins associated with lymphocytes.

BACKGROUND OF THE INVENTION

Cytolytic lymphocytes (CTLs), which include cytotoxic T cells and natural killer cells, can recognize and eliminate a wide variety of virus-infected or transformed target cells. The molecular mechanisms used by these cells to induce target cell death are incompletely understood. A large body of experimental evidence supports the granule exocytosis model, in which target cell recognition results in the release from the CTL of dense-cored cytoplasmic vesicles containing putative effector molecules such as perforin and the serine proteases (Martz et al., Immunol. Today 10:79–86, 1989; Tschopp and Nabholz, Annu. Rev. Immunol. 8:279, 1990; Young and Liu, Immunol. Today 9:140–144, 1988). Perforin has been shown to be directly cytolytic (Hameed et al., J. Exp. Med. 169:765–777, 1989; Lichtenheld et al., Nature 335:448–451, 1988; Shiver and Henkart, Cell 64:1175–1181, 1991). After inserting into target cell membranes, it polymerizes to form non-specific ion channels through which markers of intracellular compartments can readily pass (Tschopp et al., Nature 337:272–274, 1989; Young et al., Proc. Natl. Acad. Sci. 83:150–154, 1986; Yue et al., Mol. Immunol. 24:647–653, 1987). The formation of these ion channels appears to be sufficient to induce the lysis of certain cell types. Although purified serine proteases are not directly cytotoxic, the ability of protease inhibitors to block lymphocyte-mediated cytolysis suggests that these granule components might also play a role in target cell killing (Lavie et al., J. Immunol. 135:1470–1476, 1985; Rodgers et al., J. Immunol. 140:564–570, 1988).

In addition to perforin-mediated cytolysis, considerable evidence suggests that target cell death can also result from the induction of an endogenous pathway of programmed cell death. Central to this autolytic pathway is the activation of an endogenous endonuclease that results in the degradation of target cell DNA into integer multiples of a 200 bp nucleosome-sized monomer (Duke et al., Proc. Natl. Acad. Sci. U.S.A. 80:6361–6365, 1983; Wyllie, Nature 284:555–556, 1980). The resulting "ladder" of DNA fragments is considered to be characteristic of this programmed suicide pathway. Isolated CTL granules have been shown to induce both cell lysis (measured by the release of $^{51}Cr$) and DNA fragmentation (measured by the appearance of nucleosome-sized DNA fragments) in target cells (Allbritton et al., J. Exp. Med. 167:514–527, 1988; Podack and Konigsberg, J. Exp. Med. 160:695–710, 1984). However, studies which used purified perforin have shown that it, while capable of inducing cell lysis, does not induce DNA fragmentation in target cells (Duke et al., J. Exp. Med. 170:1451–1456, 1989).

SUMMARY OF THE INVENTION

The protein referred to herein as the TIA-1 antigen is a naturally-occurring compound that was first identified in association with cytoplasmic granules in cytolytic T lymphocytes and natural killer (NK) cells, using the monoclonal antibody (mAb TIA-1) produced by the hybridoma deposited in the American Type Culture Collection (ATCC) as ATCC number HB 10319. Initially identified as a 15 kD protein having various larger isoforms also immunologically reactive with the mAb of the invention, cDNAs encoding the 15 kD isoform as well as the 40 kD isoform have been cloned, sequenced, and expressed in transfected cells; these cDNAs are identified herein as SEQ ID NO.:2 and SEQ ID NO.:1, respectively. As used herein, the phrase "immunologically reactive" means that the antibody and antigen bind to each other (i.e., form an immune complex) with sufficient specificity to permit immunoassay of the antigen or antibody under standard conditions. The phrase does not necessarily exclude the possibility that the antibody binds other antigens: e.g., multimers of the antigen or related proteins as described below.

The invention features an isolated DNA that includes a sequence encoding a polypeptide with which the monoclonal antibody produced by the hybridoma designated ATCC #HB 10319 is immunologically reactive. The term "isolated DNA" is intended to denote a DNA which has been engineered so that the polypeptide-encoding sequence it includes is not flanked by the genes which, in the naturally-occurring genome of the organism from which such polypeptide-encoding sequence was derived, normally flank such sequence. This may be accomplished, for example, by creating a cDNA from a mRNA template, or by cloning a fragment of genomic DNA. The polypeptide encoded by this isolated DNA may, for example, be approximately 40 kD or 15 kD on SDS-PAGE, and may have an amino acid sequence substantially identical to that encoded by the plasmid deposited in the ATCC with ATCC #68202; the DNA may include, for example, a nucleotide sequence substantially identical to SEQ ID NO.:1 or SEQ ID NO.:2. Alternatively, the isolated DNA of the invention may be characterized as including a sequence which hybridizes under stringent conditions (e.g., as described in Sambrook et al., Molecular Cloning: A Laboratory Manual; Cold Spring Harbor Laboratory, Cold Spring Harbor, N.Y., 1989) to a nucleic acid probe which includes at least a six-nucleotide segment (preferably at least 10 nucleotides, and more preferably at least 20) of the coding sequence of the plasmid designated ATCC #68202.

Also within the invention is a vector (e.g., a plasmid such as that deposited as ATCC #68202) or a purified preparation thereof, which vector includes the isolated DNA of the invention. Once this vector is inserted into a cell such as E. coli, yeast, or a mammalian cell, the resulting cell which bears the isolated DNA of the invention (or an essentially homogeneous population of cells made up of the progeny of such a cell) may be cultured under conditions permitting expression of the isolated DNA, and the protein so expressed may be recovered from the medium or the cells, using standard methods. A substantially purified preparation of natural or recombinant TIA-1 antigen [whether 40 kD, 15 kD, or another isoform of the human protein, or a related protein from another animal, or a non-natural, genetically-engineered form which differs from the natural protein by one or more (but less than 20%) of its amino acid residues, or which is conjugated to another protein such as an antibody or a ligand] is useful for inducing the suicide pathway within a cell (preferably an immunological cell). This method of killing a cell is accomplished by contacting a cell with TIA-1 antigen in such a way as to introduce the TIA-1 antigen into the cell, where it triggers the degradation of the cell's DNA.

A probe which includes a sequence identical to a segment of at least six nucleotides (preferably at least 10, and more preferably at least 20) of the isolated DNA of the invention (e.g., a segment of SEQ ID NO.:1 or SEQ ID NO.:2, the coding sequence of the plasmid deposited as ATCC #68202) may be used in a method of identifying cytolytic lymphocytes in a biological sample (e.g., from a human), which method includes the steps of contacting RNA from the sample with the probe under conditions which permit hybridization of the probe to complementary RNA, and determining whether the probe hybridizes to the cell's RNA, wherein such hybridization is indicative of the probable presence of cytolytic lymphocytes in the sample. Alternatively, the presence of mRNA complementary to a segment of the isolated DNA of the invention can be detected in a sample by the use of two segments of the isolated DNA of the invention as primers for polymerase chain reaction (PCR), using standard PCR techniques. The ability to monitor the presence of cytolytic lymphocytes will provide an early warning of the presence of an infective agent, such as the HIV virus, in a patient. cDNA probes and PCR primers capable of detecting nucleic acid encoding the novel effector protein, TIA-1 antigen, provide an especially sensitive means of detecting the early presence of such agents.

Other features and advantages of the invention will be apparent from the following detailed description, and from the claims.

DETAILED DESCRIPTION

The drawings are first described.

FIGS. 1A and 1B are representations of the nucleotide sequence of 2G9.4 (SEQ ID NO.:1), a cDNA encoding rp40-TIA-1 (the 40 kD TIA-1 antigen), and predicted amino acid sequence of the encoded protein.

FIG. 2 is a representation of the nucleotide sequence of T4T8.9-5 (SEQ ID NO.:2), a cDNA encoding rp15-TIA-1 (the recombinant 15 kD TIA-1 antigen), and predicted amino acid sequence of the encoded protein. This cDNA was deposited in the ATCC as a plasmid designated ATCC #68202.

Figure 8:
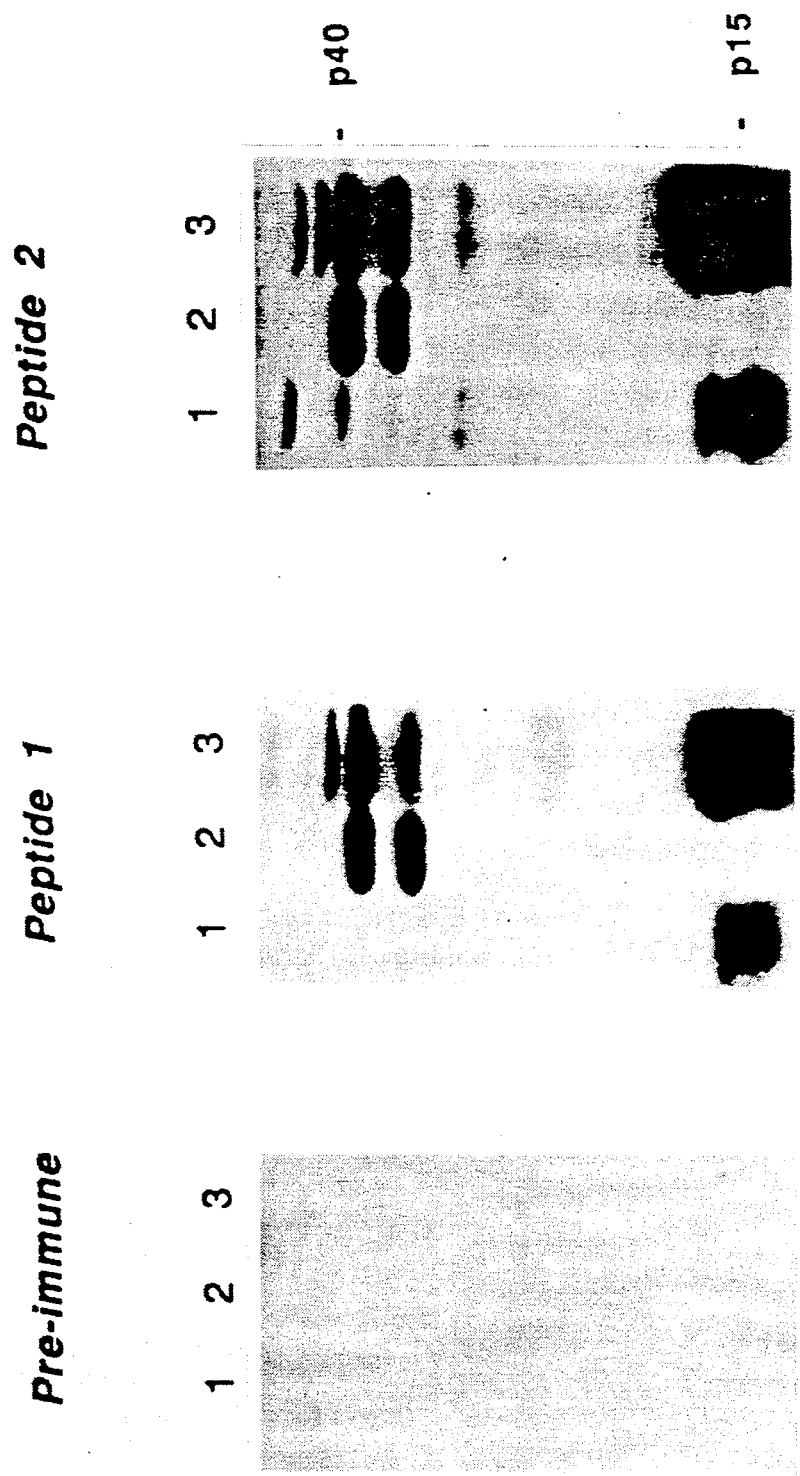

FIG. 8 is an immunoblot of an SDS-PAGE analysis of affinity-purified natural and recombinant TIA-1 antigen probed with either pre-immune rabbit sera (left panel) or anti-peptide anti-sera directed against peptide 1 [amino acids 288–307 of 2G9.4 (SEQ ID NO.:1); middle panel] or peptide 2 [amino acids 384–367 of 2G9.4 (SEQ ID NO.:1); right panel].

Figure 9:
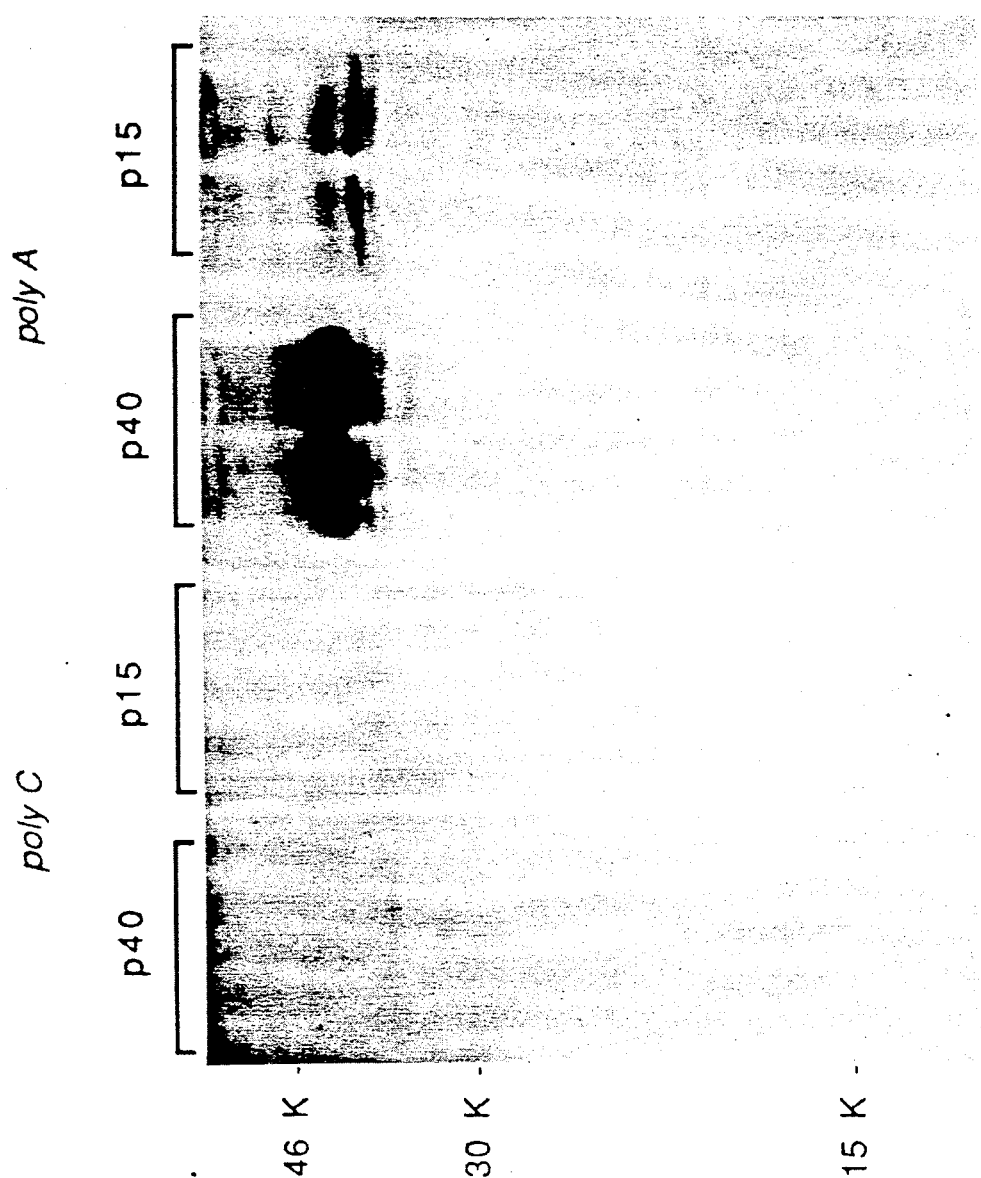

FIG. 9 is an autoradiogram of an SDS-PAGE analysis of $^{35}$S-methionine-labelled lysates from Cos cells transfected with 2G9.4 (SEQ ID NO.:1) or T4T8.9-5 (SEQ ID NO.:2) cDNA, which lysates were precipitated with either poly(C)-agarose or poly(A)-agarose in order to detect nucleic acid-binding activity of the recombinant protein.

Figure 10:
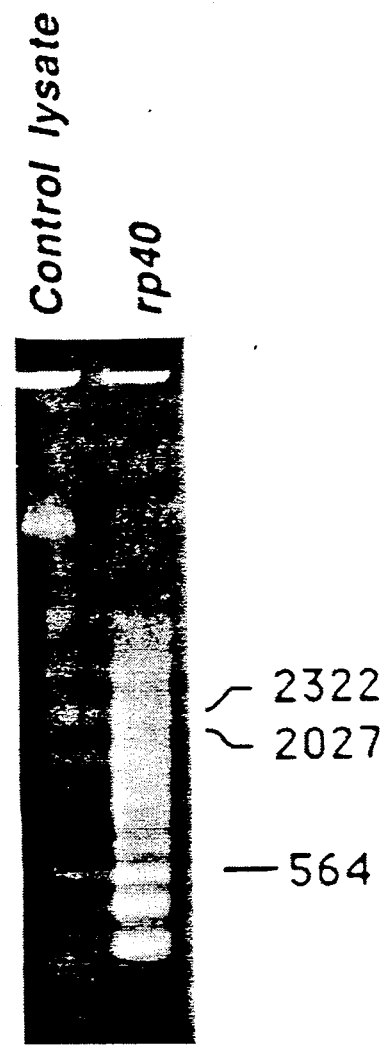

FIG. 10 is an analysis of the fragmentation of thymocyte DNA by E. coli-derived rp40-TIA-1, using electrophoresis on agarose gel to separate the DNA fragments.

Figure 11:
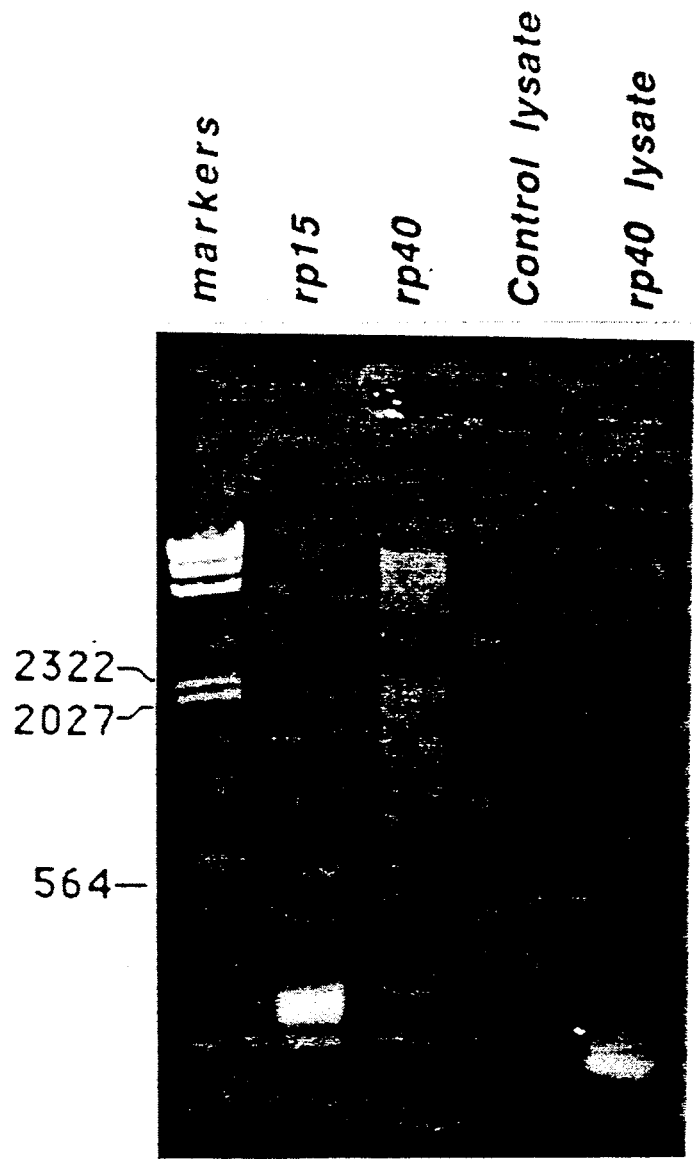

FIG. 11 is an analysis of the fragmentation of DNA in permeabilized thymocytes by rp15-TIA-1, rp40-TIA-1, and a control E. coli lysate, using electrophoresis on agarose gel to separate the DNA fragments.

Figure 12:
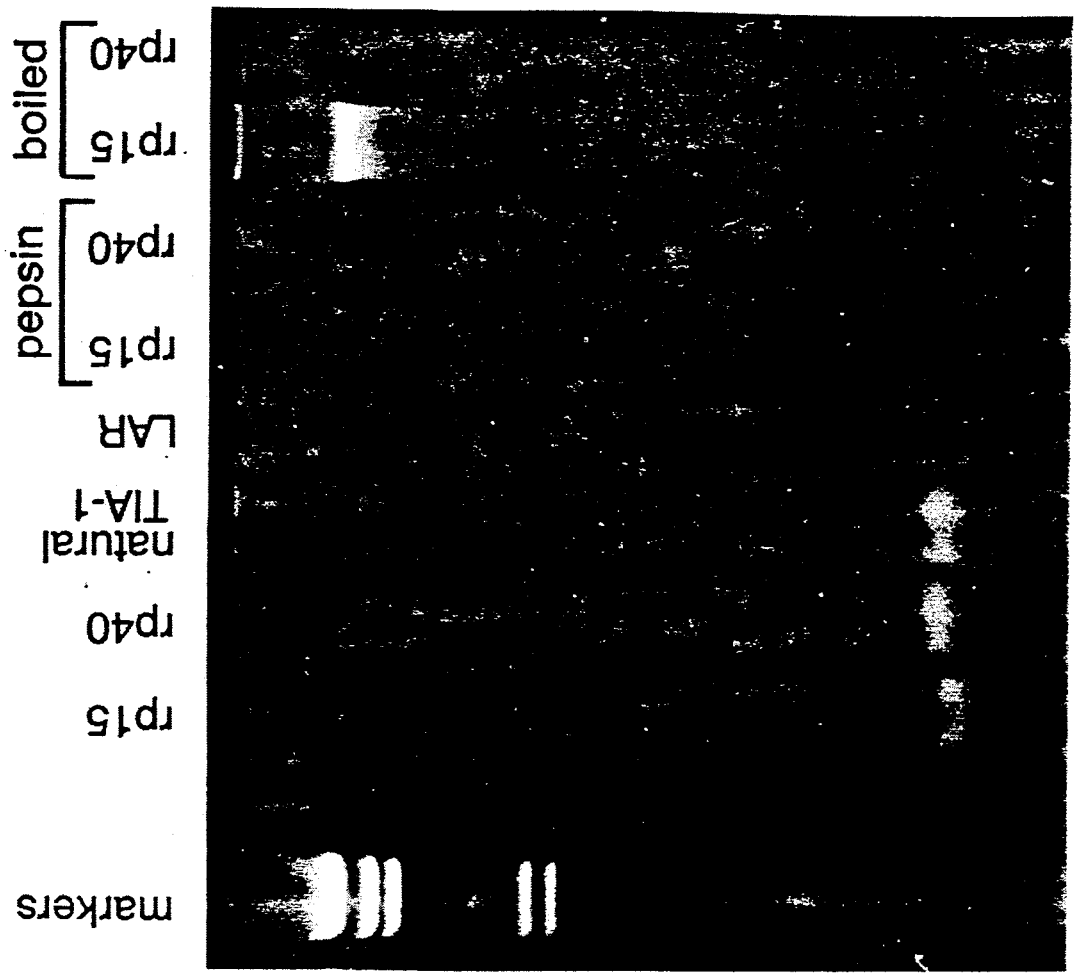

FIG. 12 is an analysis of the fragmentation of DNA in permeabilized thymocytes by rp15-TIA-1, rp40-TIA-1, natural TIA-1 antigen, E. coli-derived rLAR, and pepsin-treated or boiled rp15-TIA-1 and rp40-TIA-1, using electrophoresis on agarose gel to separate the DNA fragments.

Figure 13:
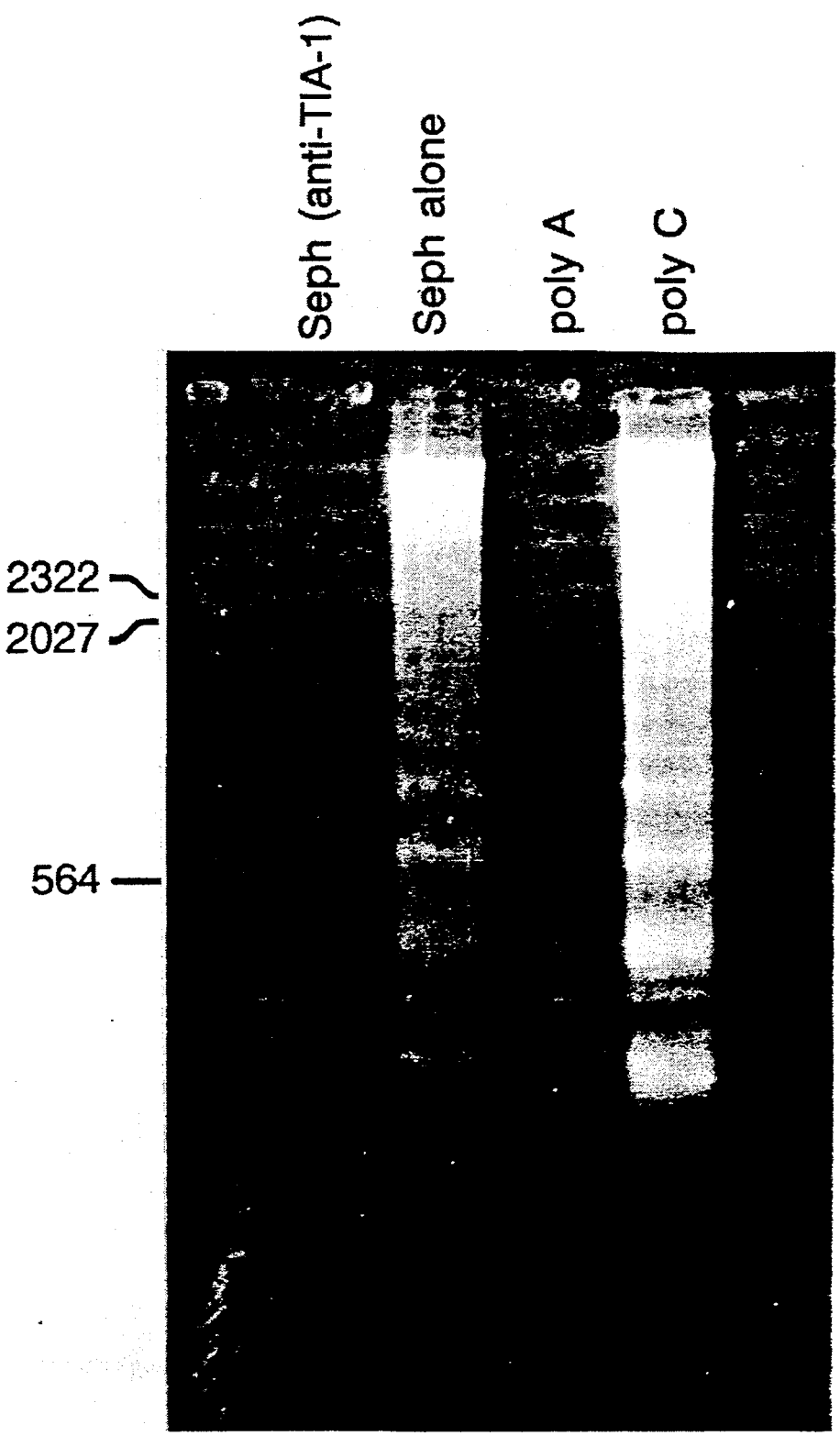

FIG. 13 is an analysis of the fragmentation of DNA in permeabilized thymocytes by rp40-TIA-1 pre-cleared with sepharose-immobilized mAb TIA-1, sepharose beads alone, immobilized poly(C), or immobilized poly(A), using electrophoresis on agarose gel to separate the DNa fragments.

Figures 14A, 14B:
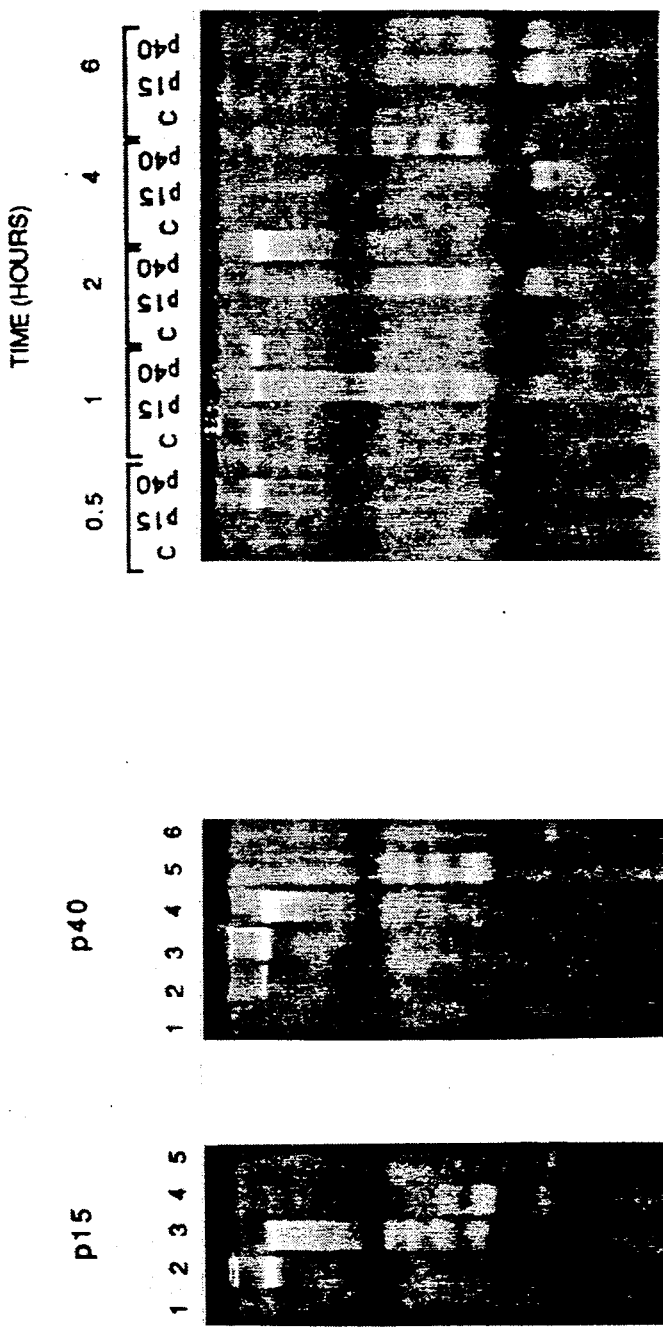

FIGS. 14A and 14B are dose response (A) and kinetic (B) analysis of DNA fragmentation by rp15-TIA-1 and rp40-TIA-1 in permeabilized thymocytes.

Figure 15A:
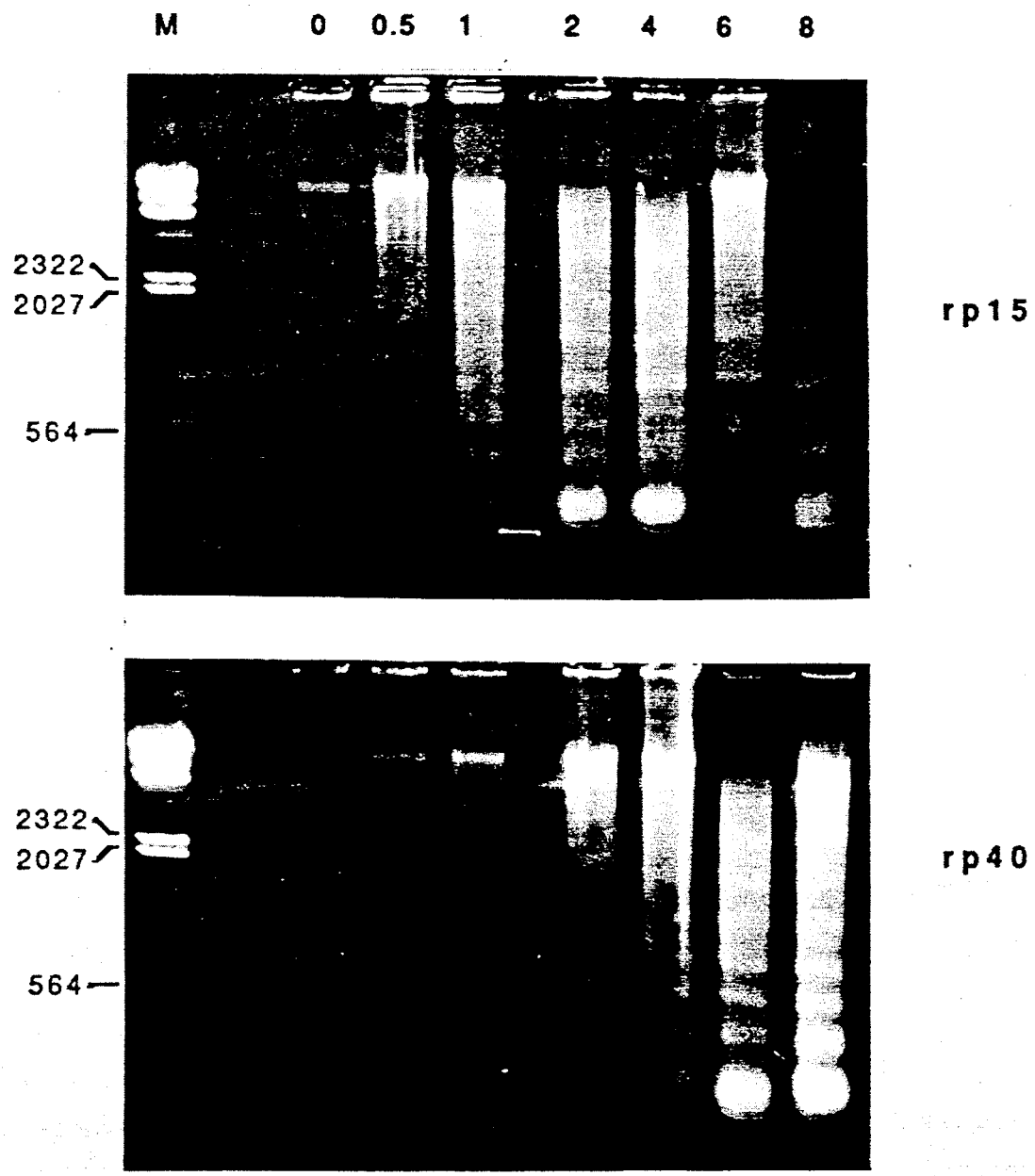
Figure 15B:
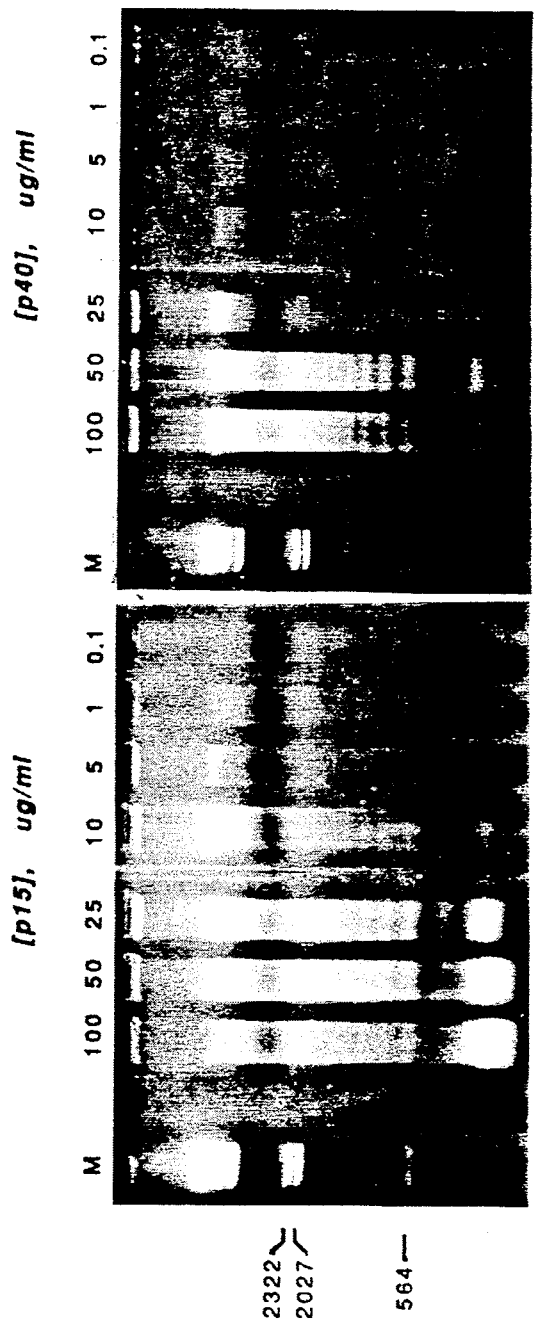

FIGS. 15A and 15B are dose response (A) and kinetic (B) analysis of DNA fragmentation by rp15-TIA-1 and rp40-TIA-1 in permeabilized peripheral blood lymphocytes (PBLs).

Figure 16:
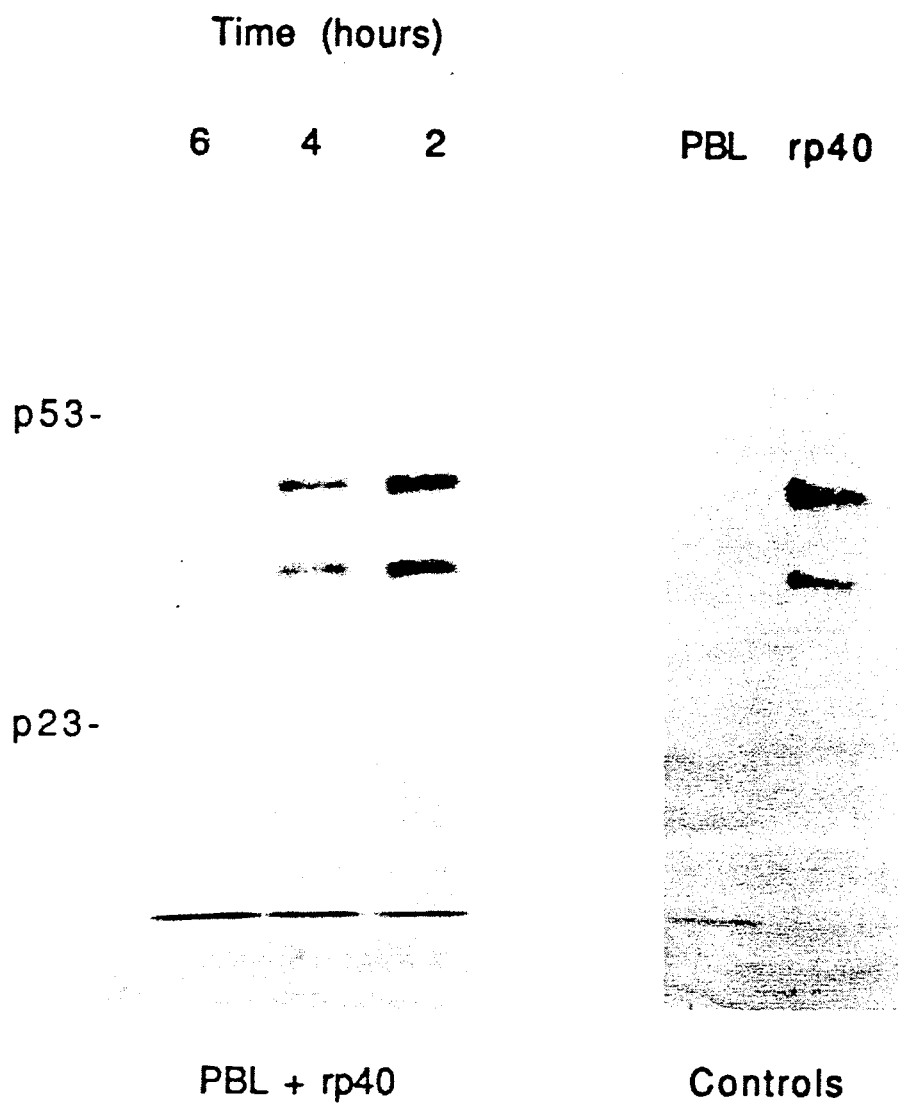
Figure 17:
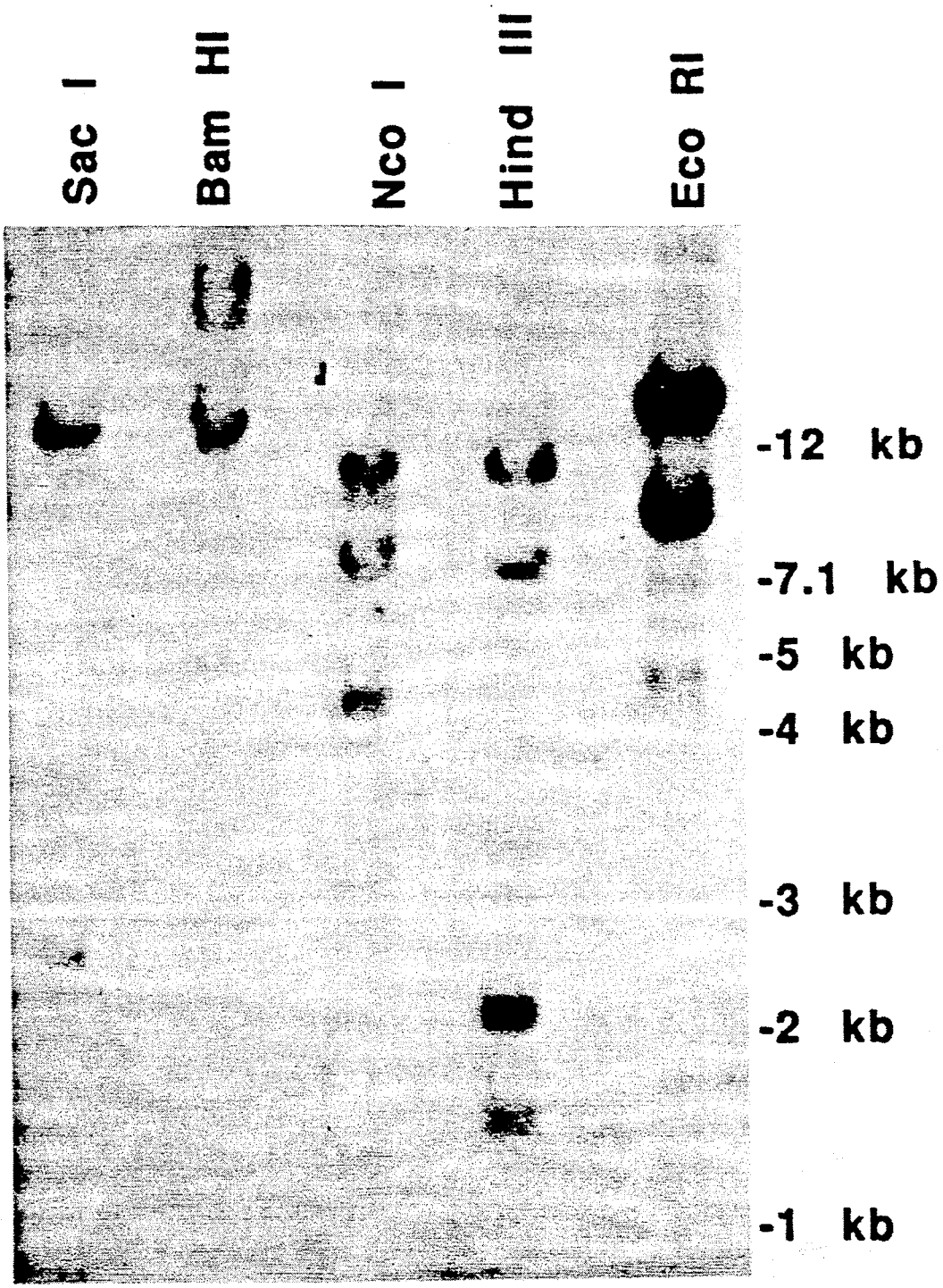

FIG. 16 is an SDS-PAGE analysis of the progressive conversion of rp40-TIA-1 from the 40 kD and 38 kD forms into a 15 kD form upon incubation with permeabilized PBLs.

Method of Isolation of mAb TIA-1

Monoclonal antibody TIA-1, the subject of U.S. Ser. No. 460,678, herein incorporated by reference, was selected as differentiating between permeabilized and unpermeabilized T cells. TIA-1 recognizes a 15 kD intracellular protein, the 15 kD TIA-1 antigen, which is found in a subpopulation of CD8+ lymphocytes from peripheral blood mononuclear cells, as well as in natural killer cells. TIA-1 antigen is observed by immunoelectron microscopy to be associated with the membrane of cytoplasmic granules in cytolytic T lymphocytes.

Hybridomas suitable to be screened for production of antibodies reactive with intracellular antigens were prepared by immunizing 6-week-old Balb/c mice with permeabilized T lymphocytes (25–30×10$^6$) at 21 day intervals over a 9–12 week period. The immunogen was prepared using Ficoll purified peripheral blood mononuclear cells obtained from plateletpheresis residues that were rosetted with sheep erythrocytes (Lay et al., Nature 300:267, 1971). Purified T lymphocytes were washed three times in PBS, resuspended at 5×10$^6$ cells/ml and permeabilized by the addition of digitonin (10 μg/ml) for 5 minutes on ice. The adequacy of permeabilization was monitored by determining trypan blue uptake, which was typically greater than 90%.

Permeabilized lymphocytes were pelleted, resuspended at 25–30×10⁶ cells/ml in sterile PBS, and injected intraperitoneally into Balb/c mice. Splenocytes from immunized mice were fused to NS-1 myeloma cells for the production of hybridomas (Konler et al., Nature 256:495, 1975).

Individual clones of the hybridomas as prepared above were screened for reactivity to permeabilized T lymphocytes by a modification of the flow cytometric method. In order to permeabilize the cells without causing undue cellular damage or the excessive loss of intracellular constituents and in order to protect the permeabilized cells against disintegration during the many washes required in preparation for flow cytometric analysis, T lymphocytes purified by sheep erythrocyte rosetting were first stabilized by mild fixation with 0.01% formaldehyde in PBS for 20 minutes on ice. Cells were then washed four times with ice cold PBS, resuspended at 5×10⁶ cells/ml in PBS and permeabilized by the addition of digitonin (10 µg/ml) for 5 minutes on ice. After the adequacy of permeabilization had been confirmed by trypan uptake, cells were pelleted and resuspended in PBS at 20×10⁶ cells/ml. Hybridoma supernatants were added to permeabilized cells in a 1:1 ratio. After 30 minutes on ice, cells were washed three times with PBS containing 0.05% Tween-20 to remove unbound antibody, further incubated with goat anti-mouse-FITC, washed, resuspended in PBS and 1% formaldehyde, and analyzed flow cytometrically, using an Epics 752 flow cytometer.

Specificity of Expression of TIA-1 Antigen

Activated T lymphocytes can contain CD4 or CD8, as well as other cell surface proteins. Purified populations of CD4+ and CD8+ lymphocytes were found to contain the TIA-1 antigen preferentially in the CD8+ subset. In an antibody binding assay of permeabilized cells, TIA-1 stained 6±2% of CD4+ cells and 55±7% of CD8+ cells. TIA-1 antigen is also expressed in natural killer (NK) cell clones, but not in immortalized T cell lines (Jurkat, HPB-ALL, CEM, HUTL-78), nor in B cell lines (Daudi, BJAB, Raji). (See Table below).

TABLE

Flow cytometric analysis of TIA-1 antigen expression in permeabilized hematopoetic cells.

| Cell Type | Relative Expression |
|---|---|
| B cells | − |
| T clls | + |
| CD4+ T cells | +/− |
| CD8+ T cells | +++ |
| Thymocytes | − |
| Con A activated thymocytes | + |
| JJ1 (NK clone) | +++ |
| CNK6 (NK clone) | +++ |
| JT 18 (NK clone) | +++ |
| YT$^B$ (NK cell leukemia) | + |
| T4T8Cl (CD+, CD8+ clone) | +++ |
| A2p (CD8+ cell line) | ++ |
| M (CD4+ clone) | + |
| MM (CD4+ clone) | + |
| N (CD4+ clone) | +/− |
| P (CD4+ clone) | + |

Effect of T Cell Activation on TIA-1 Antigen Expression

When peripheral blood T lymphocytes are cultured in the presence or absence of activating stimuli in Roswell Park Memorial Institute (RPMI) medium supplemented with 10% fetal calf serum, unstimulated T cells express a 15 kD protein that reacts with mAb TIA-1 on an immunoblot. Cells cultured over an 8 day period in the absence of activation stimuli progressively lose their ability to express the 15 kD protein, while acquiring a 28 kD immunoreactive species. In the presence of phorbalmyristic acetate (PMA), the expression of both forms of TIA-1 antigen is decreased. The T cell mitogen, Con A, induces the expression of large amounts of both the 15 kD and the 28 kD immunoreactive forms.

In addition, two higher molecular weight species appear after 6 days in culture with Con A. Antibodies reactive with CD3 similarly induce the expression of these higher molecular weight forms of TIA-1-reactive antigen, while phytohemaglutinin tends to diminish expression of TIA-1-reactive antigens. The high molecular weight immunoreactive species appear to be disulfide-linked multimers of the 15 kD monomer. When cell lysates prepared from 6 day Con A-activated T cells are separated by SDS-PAGE under reducing conditions, and then subjected to immunoblotting with mAb TIA-1, the 28 kD isoform is reduced to 15 kD, suggesting that it is a disulfide-linked dimer that includes the 15 kD species.

Intracellular Localization of TIA-1 Antigen

The intracellular location of the TIA-1 antigen was determined by rupturing cells with nitrogen cavitation and fractionating the lysate in a Percoll gradient. A similar analysis of cultured cytolytic T lymphocytes has demonstrated the presence of high density granules that contain such cytolytic effector molecules as serine proteases and perforin (Pasternack et al., Nature 322:740, 1986). When a cloned CD8+ cell line (T4T8Cl) possessing cytolytic activity was fractionated in this manner, two peaks of serine protease activity were observed. When the Percoll gradient fractions were examined by immunoblotting for the presence of mAb TIA-1-reactive material, the majority was found in the low-density membrane fraction, which also contained serine protease activity. [The low-density membrane fraction is believed to contain less mature cytolytic granules, still in the process of forming (Henkart et al., J. Immunol. 139:2398, 1987).]

Upon examination with immunoelectron microscopy, TIA-1 antigen was found to be localized within specific compartments within T4T8Cl cells, but not at the cell surface, whether in coated pits or along the plasma membrane. No label was apparent within the rough endoplasmic reticulum or the Golgi apparatus. Intense labeling was found within the first post-Golgi compartment; on membranes or endosome-like structures possessing electron-lucent cores; around the membranes of electron-dense lysosomal granules; and around membranes of small microvesicles contained within small, multi-vesiculate bodies. Both the electron-lucent endosomes and the electron-dense vesicles were labelled on their membranes. Some cytoplasmic vesicles appeared to be in transition from electron-lucent to electron-dense structures. In all cases, labelling appeared to be associated with compartment membranes only. TIA-1 antigen appears to be a specific marker of developing cytoplasmic granules.

Comparison of TIA-1 Antigen with Known Proteins

In its tissue distribution, subcellular localization and biochemical structure, TIA-1 antigen resembles several known cytolytic effector molecules. Structures such as tumor necrosis factor (TNF) and lymphotoxin (LT) (Krigler et al., Cell 53:45, 1988; Yamamoto et al., J. Immunol. 137: 1878, 1986; Schmid et al., Proc. Natl. Acad. Sci. U.S.A. 83: 1881, 1986) are about the same size as TIA-1 antigen, and could conceivably share its tissue distribution and intracellular localization. However, when the reactivity of mAb TIA-1 was tested with human TNF and lymphotoxin by immunoblotting, neither TNF nor LT were recognized by this antibody. To determine if the TIA-1 antigen might be a previously undescribed serine protease, T4T8Cl lysates were analyzed by the method of Ferguson et al. (J. Exp. Med. 167: 528, 1988). While SDS-PAGE of whole cell lysates revealed bands with serine protease activity migrating at around 30 kD, the $^3$H-diisopropyl phosphofloridate-labeled material was not reactive with mAb TIA-1, suggesting that the TIA-1 antigen is not a serine protease.

Molecular Cloning of TIA-1 Antigen

RNA from the cytolytic T cell clone T4T8Cl, which expresses high levels of TIA-1 antigen (see the Table above) was used for the construction of a cDNA library in λgt11. When this expression library was screened using TIA-1 monoclonal antibody, several bacteriophage expressing immunoreactive fusion proteins were identified. These bacteriophage were purified over three rounds of antibody selection, and the recombinant phage were expanded in plate lysates as described (Sambrook et al., A Laboratory Manual, Cold Spring Harbor Laboratory, Cold Spring Harbor, N.Y., 1989). Insert DNA was isolated from the plaque-purified recombinant phage and subcloned into the pSP65 plasmid vector. Cross hybridization analysis identified three independent clones containing related cDNAs. The largest cDNA insert (1.6 kb) was then used to probe the original library for the isolation of full length cDNAs. Five cross-reactive phage isolates were identified, each of which contained a 1.6 kb insert DNA. Although the length of the poly(A) tail differed in each of these isolates, they were identical at their 5' ends. When this same cDNA probe was used to screen a second λgt11 cDNA library prepared from PHA-activated T cells, several 2.2 kb insert cDNAs were isolated. The DNA sequence of the 2.2 kb cDNA (2G9.4; SEQ ID NO.:1), as well as the predicted amino acid sequence of a 42,000 dalton protein (subsequently referred to as rp40-TIA-1 because of its apparent migration on SDS-PAGE) encoded by the 1125 bp open reading frame, is shown in FIG. 1. The 1.6 kb cDNA (T4T8.9-5, shown in FIG. 2; SEQ ID NO.:2) was found to be identical in sequence to the last 1618 bp of the 2.2 kb cDNA (beginning at nucleotide 555 in FIG. 1, SEQ ID NO.:1). It is presently unclear whether the 1.6 kb cDNA is derived from an mRNA species distinct from that represented by the 2.2 kb cDNA. The 1.6 kb cDNA itself can encode a 16,000 dalton protein (subsequently referred to as rp15-TIA-1 because of its apparent migration on SDS-PAGE), assuming that the ATG at nucleotide position 688 (FIG. 1; SEQ ID NO.:1) is used as the protein synthesis initiation site (Kozak, 1984).

Figures 3, 4:
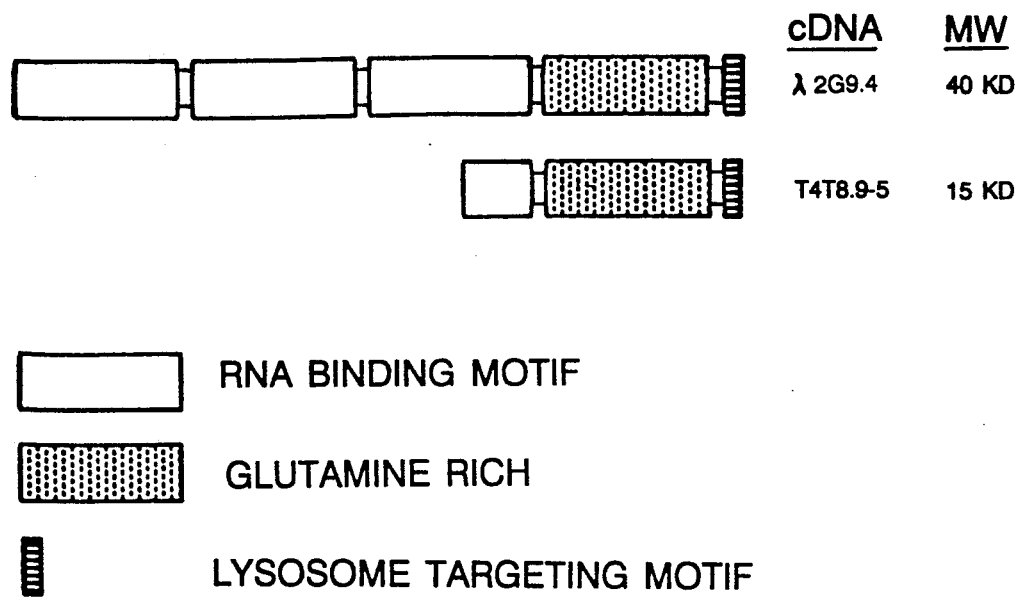
FIG. 3 is a schematic representation of protein domains included in rp40-TIA-1 and rp15-TIA-1 encoded by cDNAs 2G9.4 (SEQ ID NO.:1) and T4T8.9-5 (SEQ ID NO.:2), respectively.
FIG. 4 is a comparison of the carboxy-terminal lysosomal targeting motif of TIA-1, LAMP-1, and lgp120, with the critical tyrosine residue depicted in bold face type, and identical residues enclosed within a box.

A comparison of the predicted amino acid sequence of rp40-TIA-1 (SEQ ID NO.:1) with known sequences included in the NBRF protein database revealed significant homology to a family of RNA-binding proteins. These proteins have been shown to contain between one and four RNA-binding domains of approximately 90 amino acids expressed in association with a carboxy terminal auxiliary domain which has been postulated to be involved in protein:protein interactions (Bandziulis et al., Genes and Devl. 3:431–437, 1989). As shown in FIG. 3, rp40-TIA-1 possesses three RNA-binding domains at its amino terminus. Each RNA-binding domain includes two ribonucleoprotein consensus octapeptide sequences (RNP 1 and RNP 2) which are particularly conserved in RNA-binding proteins.

Figure 5:
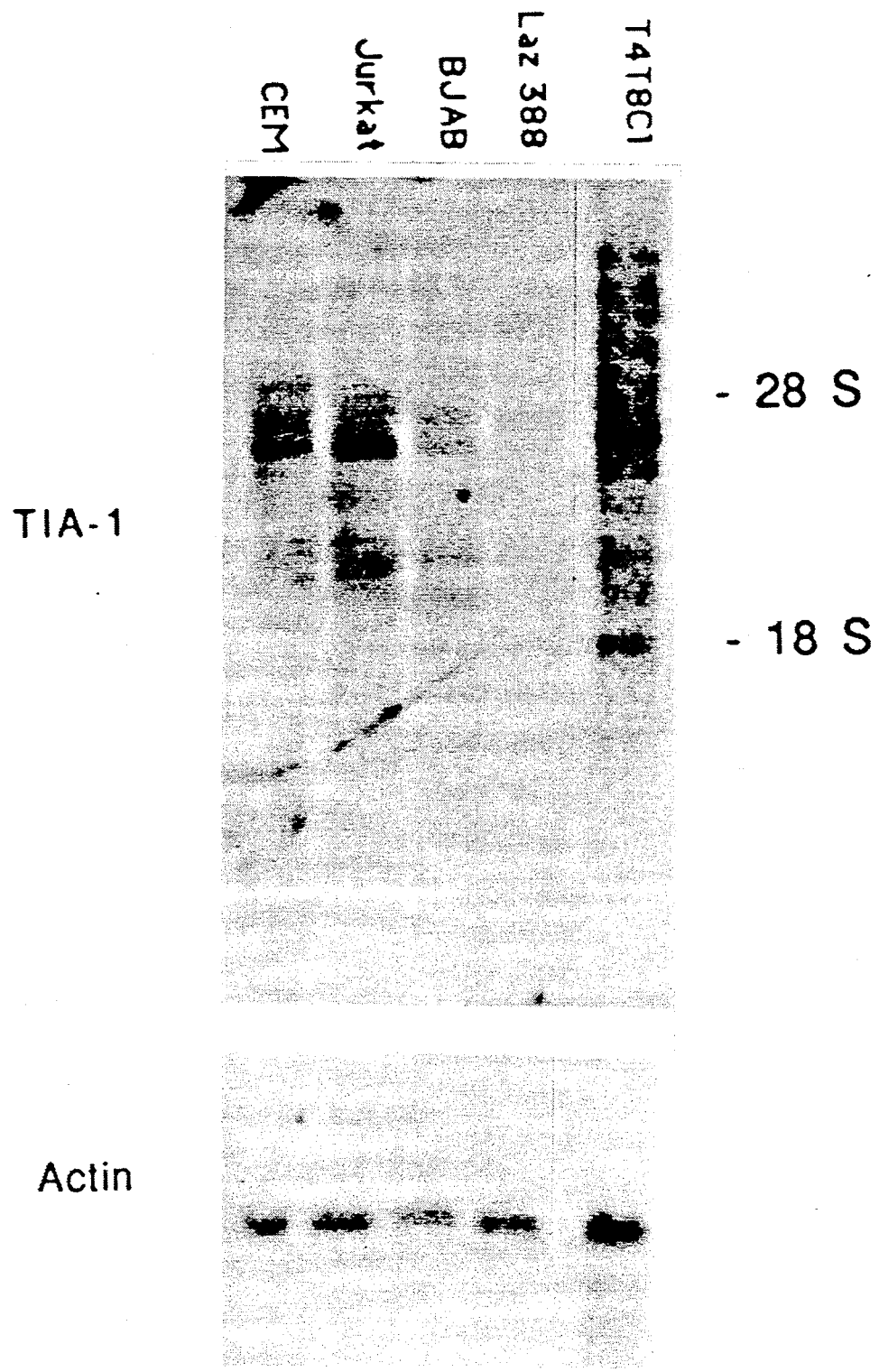
FIG. 5 is a Northern blot analysis of TIA-1 antigen mRNA expression in various cell types.

Although neither rp40-TIA-1 nor rp15-TIA-1 contains hydrophobic domains likely to span a lipid bilayer, their common carboxy-terminal domain contains a consensus sequence that has been shown to be conserved in lysosomal membrane proteins such as lamp-1 and lgp120 (Chen et al., J. Biol. Chem. 263:8754–8758, 1988; Howe et al. Proc. Natl. Acad. Sci. 85:7577–7581, 1988) (FIG. 4). A tyrosine residue located four amino acids from the carboxy-terminus has been shown by mutational analysis to be critical for the lysosomal targeting of lamp-1 (Williams and Fukuda, J. Cell. Biol. 111:155–966, 2990). The presence of this structural motif in rp40-TIA-1 and rp15-TIA-1 is of interest because, as described above, immunoelectron microscopy has localized TIA-1 antigen to the membranes of cytolytic granules in CTLs and NK cells. The remainder of the carboxy-terminal, non-RNA-binding region of rp40-TIA-1 is relatively glutamine-rich, and is most closely related to the human prion protein (Prusiner, Annu. Rev. Microbiol. 43:345–374, 1989), with which it shares a 26% identity over an 84 amino acid region.

mRNA expression was determined by Northern blotting using a region of the cDNA encoding the carboxy-terminal auxiliary domain of rp40-TIA-1 (SEQ ID NO.:1) as a probe. As shown in FIG. 5, two predominant species of hybridizing RNA (2.7 kb and 4.0 kb) were identified in T cell lines and, to a lesser extent, in B cell lines. The cytotoxic T cell clone designated T4T8C1 also expressed these two RNA species, but, in addition, the latter cells expressed increased amounts of two smaller RNA species (1.7 kb and 2.2 kb), whose sizes were similar to the T4T8.9-5 and 2G9.4 cDNAs.

Figure 6:
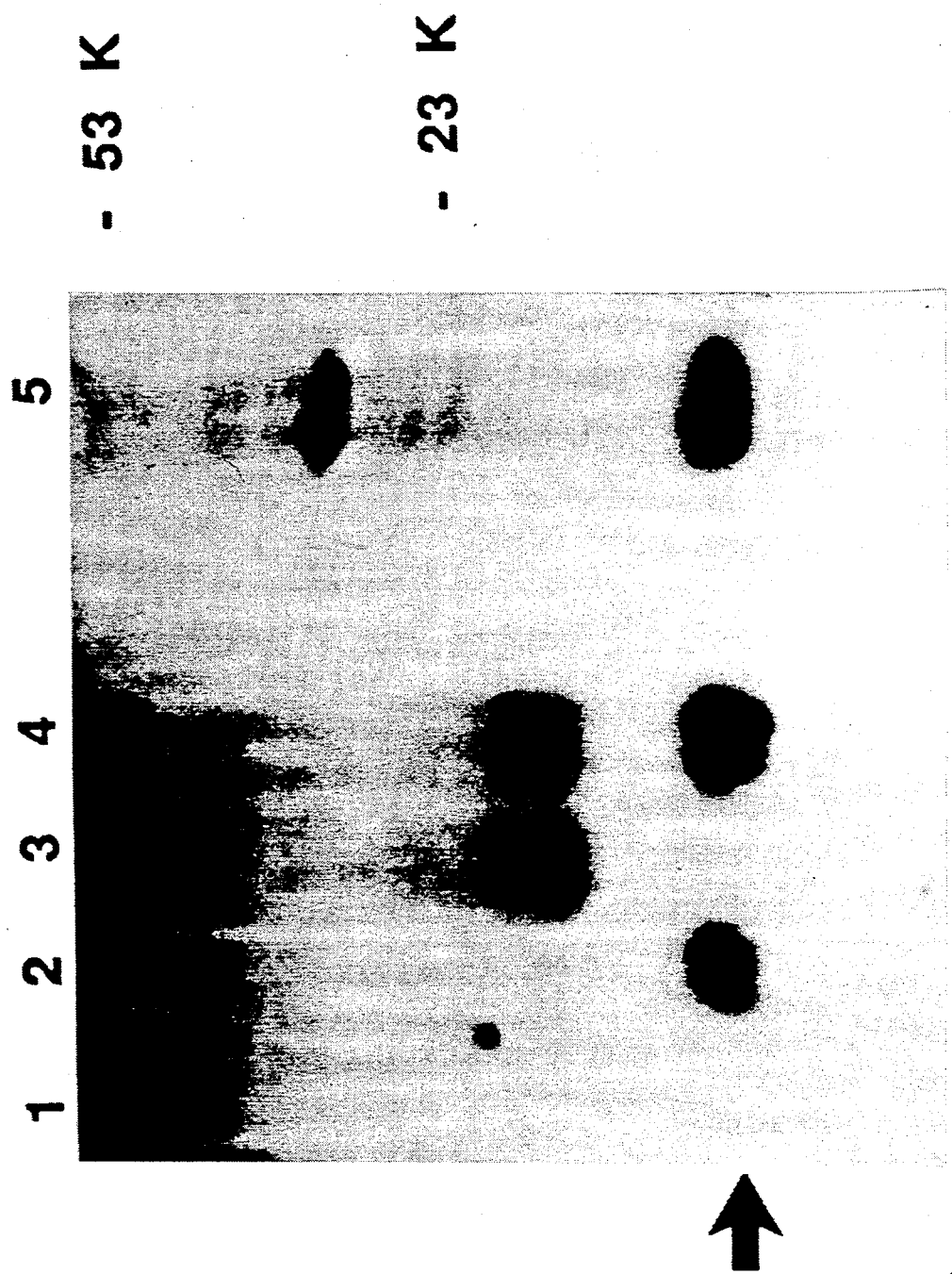
FIG. 6 is an SDS-PAGE analysis of the expression of rp15-TIA-1 in Cos cells transfected with a vector containing the T4T8.9-5 cDNA (SEQ ID NO.:2).
Figure 7:
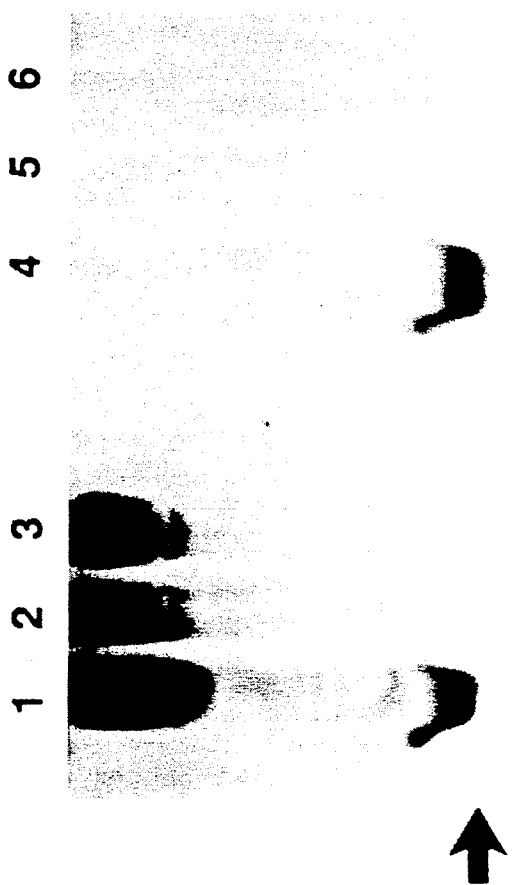
FIG. 7 is an SDS-PAGE analysis of the expression of rp40-TIA-1 in Cos cells transfected with a vector containing the 2G9.4 cDNA (SEQ ID NO.:1).

Expression and Characterization of Recombinant TIA-1 Antigen cDNAs encoding rp40-TIA-1 and rp15-TIA-1 were cloned into the pMT-2 eukaryotic expression vector (Bonthron et al., Nature 324:270–273, 1986) for transient expression in Cos cells. After three days, cells were solubilized in digitonin lysis buffer. Cell lysates were either directly applied to a 12% SDS-polyacrylamde gel (lanes 1 and 2 of FIG. 6) or first immunoprecipitated using mAb TIA-1 (lanes 3 and 4) before electrophoretic separation. Lane 5 contains the postnuclear digitonin lysate of peripheral blood lymphocytes. Following electrophoresis, the gel was transferred to nitrocellulose, probed with a monoclonal antibody reactive with TIA-1 antigen, and developed by sequential incubation with rabbit anti-mouse Ig and $^{125}$I-Protein A. Autoradiographic exposure was for 12 hours. The relative migration of molecular size markers is as indicated in FIG. 6, where it is shown that Cos cells transfected with the 1.6 kb cDNA encoding rp15-TIA-1 (T4T8.9-5; SEQ ID NO.:2) contain a 15 kD immunoreactive protein present in both cell lysates (lane 2) and immunoprecipitates (lane 4), and which comigrates with the natural 15 kD protein identified in cell lysates prepared from T cells (lane 5). Cos cells transfected with the pMT-2 vector alone did not contain this 15 kD protein (lanes 1 and 3). In the immunoprecipitates separated in lanes 3 and 4, the higher molecular weight bands are immunoglobulin heavy and light chains that are detected by the rabbit anti-mouse Ig developing antibody. FIG. 7 shows that Cos cells transfected with the 2.2 kb cDNA encoding rp40-TIA-1 (2G9.4; SEQ ID NO.:1) expressed a 40 kD immunoreactive protein that was identified in both immunoprecipitates (lane 1) and cell lysates (lane 4). Control cells transfected with the pMT-2 vector alone (lanes 2 and 5) or untransfected cells (lanes 3 and 6) did not contain this 40 kD protein.

Because the cDNAs encoding TIA-1 antigen were identified by immunoselection, it was possible that they encoded immunologically cross-reactive proteins unrelated to the 15 kD granule protein. In order to rule out this possibility, rabbit anti-peptide antibodies reactive with peptides corresponding to two different regions of rp40-TIA-1 [amino acids 288-307 (peptide 1, middle panel of FIG. 8) and amino acids 384-367 (peptide 2, right panel)] were made and used to probe nitrocellulose blots of 12% SDS-PAGE-separated recombinant and natural TIA-1 antigen. The immunoblots were developed using affinity-purified goat anti-rabbit F(ab)':-horseradish peroxidase conjugates and the ECL detection reagent (Amersham). The specificity of these antibodies for the immunizing peptides was confirmed by ELISA (not shown). The original monoclonal antibody reactive with TIA-1 antigen did not recognize either of the synthetic peptides. Pre-immune sera pooled from the two rabbits used for the production of anti-peptide antisera failed to recognize rp15-TIA-1 (lane 1), rp40-TIA-1 (lane 2), or natural TIA-1 antigen (lane 3) in immunoblots (FIG. 8, left panel). In contrast, both anti-peptide sera (FIG. 8, middle and right panels) recognized rp15-TIA-1 (lane 1), rp40-TIA-1 (lane 2) and natural TIA-1 antigen (lane 3). This result provides strong evidence for the identity of the natural and recombinant proteins recognized by the TIA-1 mAb.

To determine the specificity of the RNA-binding domain of rp40-TIA-1, Cos cells were transfected with either T4T8.9-5 (SEQ ID NO.:2) or 2G9.4 (SEQ ID NO.:1) cDNA. After three days, cells were metabolically labeled with $^{35}S$ methionine for four hours in methionine-free medium, washed, and solubilized using digitonin lysis buffer. Radiolabelled lysates were then immunoprecipitated using either poly(A)-agarose or poly(C)-agarose, separated on a 10% SDS-polyacrylamide gel, and analyzed by autoradiography. As shown in FIG. 9, in which the relative migration of $^{14}C$-labeled molecular weight standards are shown at the left, rp40-TIA-1 is specifically precipitated by immobilized poly(A), but not by immobilized poly(C). As expected from its lack of a complete RNA-binding domain, rp15-TIA-1was not precipitated by either poly(A) or poly(C). This result domonstrates that the 40 kD isoform of TIA-1 antigen is a nucleic acid binding protein which preferentially recognizes poly(A) homopolymers.

Functional Analysis of Purified Recombinant TIA-1Antigen

In order to produce quantities of recombinant TIA-1 antigen sufficient for large scale purification, cDNAs encoding rp15-TIA-1 (SEQ ID NO.:2) and rp40-TIA-1 (SEQ ID NO.:1) were cloned into the prokaryotic expression vector pT7-7 (Tabor and Richardson, Proc. Natl. Acad. Sci. 82:1074-1078, 1985). Bacterial extracts containing each recombinant protein were then purified by affinity chromatography using poly(A)-agarose and/or Sepharose-immobilized antibodies reactive with TIA-1 antigen, as described in Experimental Methods. In its tissue distribution and subcellular localization, natural TIA-1 antigen resembles several known or suspected cytolytic effector molecules. The ability of rp15-TIA-1 and rp40-TIA-1 to induce $^{51}Cr$ release from target cells was therefore directly assessed. Under conditions in which natural killer cells efficiently induced target cell lysis, neither rp15-TIA-1 nor rp40-TIA-1 caused $^{51}Cr$ release above background from pre-loaded K562 or Molt-4 target cells.

A second possible mechanism for induction of cell killing by TIA-1 antigen is via the triggering of programmed cell death in susceptible cell lines. Attempts to measure the induction of DNA fragmentation in cell lines were frustrated by the finding of fragmented DNA in untreated control cells. However, when rp40-TIA-1 was tested for its ability to induce DNA fragmentation in thymocytes, the target cell population in which programmed cell death was originally described (Wyllie, 1980), it was found that exposure of freshly isolated thymocytes to purified, $E.$ $coli$-derived rp40-TIA-1 (50 $\mu$g/ml) for 48 hours at 37° C. resulted in the appearance of nucleosome-sized DNA fragments characteristic of cells undergoing programmed cell death (FIG. 10; electrophoretic separation was on a 1.4% agarose gel, with the DNA stained with ethidium bromide for visualization under UV light; the relative migration of marker DNAs from a HindIII digest of lambda DNA are indicated). Thymocytes treated with extracts from $E.$ $Coli$ transfected with the pT7-7 vector alone (3.3 mg protein extract/ml) did not contain fragmented DNA (FIG. 10).

Because of the relatively long incubation times required to induce DNA fragmentation in intact thymocytes, it was deemed possible that this result reflected in part the natural tendency of these cells to die during prolonged in vitro culture. Therefore, the ability of $E.$ $coli$-derived TIA-1 antigen to induce DNA fragmentation in thymocytes permeabilized with digitonin was tested. FIG. 11, which includes HindIII digests of lambda DNA as size markers, shows that both rp15-TIA-1 and rp40-TIA-1 induce DNA fragmentation in permeabilized thymocytes after only 6 hours. Furthermore, crude bacterial lysates prepared from $E.$ $coli$ transfected with the pT7-7 vector alone (3.3 mg protein extract/ml) did not induce DNA fragmentation (FIG. 11). In experiments not shown, mock purification of these control lysates using Sepharose-immobilized TIA-1 antibody produced material which did not induce DNA fragmentation in permeabilized cells.

Natural TIA-1 antigen purified from peripheral blood lymphocytes by immunoaffinity chromatography was also found to induce DNA fragmentation in permeabilized thymocytes. FIG. 12 compares the DNA-degrading activity of 50 $\mu$g/ml of rp15-TIA-1, rp40-TIA-1 and natural TIA-1. Incubation was for 6 hours prior to assaying for DNA fragmentation as described in Experimental Methods. Also included in FIG. 12 are results obtained using rp15-TIA-1 and rp40-TIA-1 pre-treated with immobilized pepsin for four hours at 37° C. or boiled for 10 minutes prior to their addition to thymocytes. The relative migration of HindIII restriction fragments of lambda DNA is included in this figure for size comparison. Although the small amounts of protein present in preparations of natural TIA-1 made it difficult to estimate the purity of this material, its ability to induce DNA fragmentation provides strong evidence that the biological activity of the recombinant TIA-1 is not an artifact of the bacterial expression system. FIG. 12 also shows that a control protein, LARDI phosphatase, produced in the same bacterial expression system as rp15-TIA-1 and rp40-TIA-1, is devoid of DNA-degrading activity. Proteolytic digestion of rp15-TIA-1 and rp40-TIA-1 using agarose-immobilized pepsin resulted in loss of DNA-degrading activity, confirming that the active component is a protein (FIG. 12). Both rp15-TIA-1 and rp40-TIA-1 were similarly inactivated by boiling, suggesting that a native conformation is required for activity (FIG. 12).

Further evidence that rp40-TIA-1 was itself responsible for inducing DNA fragmentation was obtained by pre-clearing a rp40-TIA-1-containing solution four times with either sepharose beads alone, sepharose-immobilized mAb TIA-1, poly(A)-agarose, or poly(C)-agarose. The pre-cleared solutions were diluted into RPMI containing 10% FCS and incubated with digitonin-permeabilized thymocytes for 6 hours. As shown in FIG. 13, whereas rp40-TIA-1 pre-cleared with sepharose alone or with poly(C)-agarose retained DNA degrading activity, rp40-TIA-1 pre-cleared with sepharose-immobilized mAb TIA-1 or poly(A)-agarose was inactive. This result confirms that the DNA-degrading activity binds to mAb TIA-1 and to poly(A), properties expected of rp40-TIA-1.

FIG. 14A illustrates the degree of DNA fragmentation induced by different concentrations of purified rp15-TIA-1 and rp40-TIA-1 in permeabilized thymocytes incubated for six hours with the indicated dose. Lane 1: 0.1 μg/ml; lane 2: 1.0 μg/ml; lane 3: 5 μg/ml; lane 4: 10 μg/ml; lane 5: 25 μg/ml; lane 6: 50 μg/ml. In the experiment illustrated in FIG. 14B, purified rp15-TIA-1, rp40-TIA-1 or rLAR was incubated with permeabilized thymocytes at a concentration of 50 μg/ml for the indicated times prior to analyzing cells for the induction of fragmented DNA. Both rp15-TIA-1 and rp40-TIA-1 were found to induce DNA fragmentation at micromolar concentrations (FIG. 14A), although with different kinetics: whereas rp15-TIA-1 induced DNA fragmentation in permeabilized thymocytes within 1 hour, rp40-TIA-1 induced a similar degree of DNA fragmentation only after a 4 hour incubation (FIG. 14B).

Because the majority of thymocytes are thought to be pre-destined for an apoptotic death, it was considered possible that these cells had already initiated the programmed pathway that would lead to activation of the endogenous endonuclease. In order to determine whether the DNA fragmentation induced by TIA-1 is generalizable to other cell types, the dose response and kinetic experiments were repeated, using permeabilized peripheral blood lymphocytes (PBLs). Just as in thymoyctes, DNA fragmentation was found to be induced in permeabilized PBLs by both rp40-TIA-1 and rp15-TIA-1 (FIG. 15A), with the kinetics of the former significantly delayed compared to the latter (FIG. 15B). These results suggest that TIA-1 antigen is able to induce programmed cell death in lymphocytes.

The delayed kinetics of DNA fragmentation induced by rp40-TIA-1 suggested the possibility that rp40-TIA-1 might be proteolytically processed to release the biologically active 15 kD carboxy-terminal region that corresponds to the 15 kD isoform of TIA-1 antigen. Poly(A)-agarose-purified rp40-TIA-1 (10 μg) was incubated with digitonin-permeabilized PBLs (5×10⁶ cells in 00 μl RPMI) in individual wells of a 96-well round bottom tissue culture plate for the various times indicated in FIG. 16. After solubilizing cells in lysis buffer, supernatants were analyzed by SDS-PAGE and immunoblotting, which revealed the progressive disappearance of the 40 kD and 38 kD forms of rp40-TIA-1 (FIG. 16, left panel). At the same time, increasing amounts of a 15 kD protein that co-migrated with natural TIA-1 antigen (shown in the control lane containing PBL lysate alone) appeared in these immunoblots. Similar results were obtained when $^{125}$I-labeled rp40-TIA-1 was incubated with permeabilized target cells, suggesting that the appearance of the 15 kD protein did not result from its de novo synthesis by the permeabilized PBLs (data not shown). The right panel of FIG. 16 shows control samples containing cells alone or rp40-TIA-1 alone. These results suggest that PBLs express a protease capable of specifically cleaving rp40-TIA-1 at a point which results in the release of its 15 kD carboxy terminal peptide.

EXPERIMENTAL PROCEDURES

Cells

Cell lines were grown in RPMI containing 10% fetal bovine serum. Peripheral blood lymphocytes were isolated from leukopheresis residues by centrifugation over ficollhypaque (Pharmacia). Normal thymus was obtained from patients less than 6 years old who had part of their thymus removed during cardiac surgery. A single-cell suspension was obtained by mincing a portion of thymus using sterile scissors, then passing the fragments through a stainless steel mesh. These cells were centrifuged over ficoll hypaque to isolate a viable single-cell suspension of thymocytes.

Antibodies

The monoclonal antibody TIA-1 (IgG1) was produced and characterized as described above. Affinity-purified rabbit anti-mouse Ig was purchased from Jackson Immunoresearch Laboratories, West Grove, Pa. Horseradish peroxidase-conjugated goat anti-rabbit and goat anti-mouse Ig were purchased from Sigma.

Rabbit anti-peptide antibodies were prepared by coupling the indicated 20-amino acid peptides to keyhole limpet hemocyanin at an 8:1 molar ratio by the dropwise addition of glutaraldehyde to a final concentration of 7 mM, followed by a further 24 hour incubation at room temperature. After dialyzing extensively, KLH-peptide conjugates were used to immunize rabbits (1 mg peptide equivalent in complete Freund's adjuvant injected at 21-day intervals over 3 months). Pre-immune sera was obtained from each rabbit prior to the initial immunization.

Preparation of a CTL cDNA Library

Total cellular RNA was isolated from 5×10⁸ CTL cells (T4T8Cl) using the proteinase K extraction method (Sambrook et al., 1989). Poly(A)+RNA was isolated by oligo dT cellulose chromatography. cDNA was synthesized using the cDNA synthesis system (BRL), following the instructions of the manufacturer. Briefly, cDNAs were transcribed from poly(A) RNA templates using reverse transcriptase and an oligo-dT primer. After treatment with EcoRI methylase, cDNAs were ligated to EcoRI linkers and digested with EcoRI. After removing excess linker by molecular sieve chromatography, cDNAs were ligated into phosphatase-treated λgt11 arms. The resulting recombinants were packaged into phage heads using an in vitro packaging system as described by the suppliers (Amersham). The resulting library had a complexity of about $2 \times 10^6$ plaques per mg RNA and an average insert size of 1.1 kb (range 0.4-2.9).

cDNA Cloning and Secuencing

λgt11 recombinants from either the T4T8Cl library described above, or a library prepared from PHA-activated T cells (Clontech) were plated at a density of 30,000 plaques per 150 mm petrie dish onto a lawn of *E. coli* strain Y1088. After a four hour incubation at 42° C., plates were overlaid with a nitrocellulose filter saturated with isopropl-β-D thiogalactoside, essentially as described (Snyder et al., Methods in Enzymol. 154:107, 1987). After a further overnight incubation, the filters were marked for position, removed and blocked for 1-2 hours with PBS containing 3% BSA. Filters were then probed with mAb TIA-1, developed with $^{125}$I-protein A and subjected to autoradiography. Positive clones from primary screens were plaque-purified and expanded on plates of Y1088. Phage DNA was extracted from plate lysates, digested with EcoRI to liberate inserts, and subcloned into pSP65 plasmid DNA. Dideoxy sequencing using Sequenase (USB) was performed using oligonucleotide primers and alkali-denatured plasmid DNA containing the indicated inserts, as described by the suppliers.

DNA Fragmentation

Human peripheral blood mononuclear cells or thymocytes were permeabilized by suspending at $5 \times 10^6$ cells/ml in cold RPMI containing 10 μg/ml digitonin. After a 5 minute incubation on ice, cells were diluted with 10 fold excess of cold RPMI, and centrifuged at 1000 rpm for 10 minutes. Cell pellets were resuspended in RPMI and cultured in 96-well U-bottom plates in the absence or presence of the indicated additions at 37° C. in a 5% $CO_2$ incubator for the indicated times. Cells were then lysed by the addition of an equal volume of 20 mM Tris (pH 7.4), 0.4 mM EDTA, 0.4% Triton X-100. Contents of each well were transferred to a microfuge tube and centrifuged at 14,000 rpm for 5 minutes. Supernatants were collected and adjusted to contain 0.5M NaCl and an equal volume of isopropanol. After incubating overnight at $-70°$ C., samples were thawed and centrifuged at 14,000 rpm for 10 minutes, washed once with 70% ethanol, and dried in a Speed-Vac. Pellets were resuspended in 20 μl of TE buffer containing 0.1 mg/ml RNase and incubated at 37° C. for 30 minutes. After the addition of loading buffer, samples were separated on agarose gels (0.8-1.2%) and visualized under UV light.

Affinity Purification of Recombinant Proteins

*E. coli* strain BL21 (DE3) was transfected with the PT7-7 plasmid vector (Tabor and Richardson, 1985) containing either 2G9.4 (SEQ ID NO.:1) or T4T8.9-5 (SEQ ID NO.:2) insert DNA. Bacterial cultures were grown in LB media containing 100 μg/ml ampicillin to an $OD_{600}$ of 0.45, adjusted to contain 0.4% glucose and 0.4 mM IPTG, then further incubated with shaking at 30°°C. for 4 hours. Cells were harvested by centrifugation at 4000 rpm for 10 minutes and washed once with ice cold PBS; lysates were prepared following the method of Cull and McHenry (Methods in Enzymology 182:147-154, 1990).

Bacterial lysates (20 ml) were incubated with Sepharose-immobilized mAb TIA-1 (3 ml packed beads) for 2-12 hours with agitation at 4° C. Sepharose beads were transferred to a column, washed with 20 bed volumes of binding buffer (50 mM Tris, pH 8.0, 10 mM EDTA, 140 mM NaCl, 10% sucrose), and eluted with 5 bed volumes of 0.1M triethylamine (pH 12.0) collected in 1 ml fractions into tubes containing 100 μl of 1M Tris HCl, pH 6.8. Fractions containing protein were pooled and dialyzed against PBS four times at 4° C. Analysis of purified preparations of rp15-TIA-1 by Coomassie-stained polyacrylamide gel electrophoresis revealed a 15 kD band as the major protein in these preparations. Similar analysis of rp40-TIA-1 revealed three major species migrating at 40 kD, 38 kD and 15 kD. The 38 kD and 15 kD forms were recognized by mAb TIA-1, suggesting that they are degradation products of the 40 kD protein. The estimated purity of these preparations ranged between 60 and 90%, as determined by densitometric analysis.

An alternative method for the purification of rp40-TIA-1 using poly(A)-agarose as an affinity matrix was followed in some experiments. Bacterial lysates prepared as described above were first passaged over a poly(C)-agarose column for the removal of non-specifically binding material. Pre-cleared lysates were then passed through a poly(A)-agarose column, washed extensively with binding buffer, and then eluted with 1.3M guanidine HCl prepared in the same binding buffer. After dialysis and concentration, purified rp40-TIA-1 was analyzed by SDS-PAGE. Coomasi blue staining of rp40-TIA-1 revealed two prominant bands at 40 kD and 38 kD, both of which were recognized by antibodies reactive with TIA-1 antigen. The 15 kD degradation product included in preparations purified using antibody affinity chromatography was not present in poly(A)-purified material, suggesting that the 15 kD protein is derived from the carboxy terminus of the 40 kD protein. The estimated purity of these preparations ranged from 60-90% (including both p40 and p38).

Cos Cell Transfections

Cos cells were transfected with the pMT-2 plasmid (Bonthron et al., Nature 324:270-273, 1986) containing the indicated insert DNA, using the DEAE dextran method as described (Sambrook et al., 1989). After three days of culture, transfected cells were either metabolically labeled with $^{35}$S-methionine in methionine-free medium (GIBCO), or directly solubilized with digitonin lysis buffer for 30 minutes on ice. Solubilized cells were centrifuged for 30 minutes in an Eppindorf microfuge, after which supernatants were pre-cleared using protein (A)-sepharose bound to rabbit anti-mouse Ig. Immunoprecipitations were performed using 25 μl of either mAb TIA-1-sepharose, poly(A)-agarose, or poly(C)-agarose for four hours at 4° C. Beads were then washed four times with digitonin lysis buffer prior to SDS-PAGE analysis.

Immunoblotting

Immunoblotting analysis was carried out as described by Anderson et al. (J. Immunol. 144:574-582, 1990). Immunoblots developed using the monoclonal antibody TIA-1 were detected using either rabbit anti-mouse Ig (Jackson Immunochemicals) followed by $^{125}$I-protein A (New England Nuclear), or goat anti-mouse:alkaline phosphatase (Sigma) followed by BCIP and NCT (King et al., Proc. Natl. Acad. Sci. 82:4717-4721, 1985). Immunoblots developed using rabbit antisera were detected using goat anti-rabbit: horseradish peroxidase followed by an ECL light-based reagent (ECL), as described by the supplier (Amersham).

Northern Blotting

Total cellular RNA was isolated from the indicated cells as described in Sambrook et al. (1989). poly(A)+ RNA was enriched using oligo-dT cellulose chromatography (Beoringer Mannheim). Equal amounts of poly(A)+ RNA (5 μg) were separated on a 1.4% formaldehyde agarose gel as described (Sambrook et al., 1989). After transferring to nitrocellulose by passive diffusion, blots were prehybridized in 50% formamide, 5X SSC, 25 mM KPO₄, pH 7.4, 5X Denhardt's, 50 mg/ml denatured salmon sperm DNA for 4 hours at 42° C. Probe DNAs were $^{32}P$ labeled by nick translation, diluted in the above solution, and hybridized to the nitrocellulose blots for 12–24 hours at 42° C. Blots were then washed twice with 1X SSC containing 0.1% SDS prior to autoradiographic exposure. Blots were then stripped by boiling in H₂O for 10 minutes, and re-probed using a linear DNA fragment encoding actin.

Use

A probe for the detection of nucleic acid (e.g., mRNA) encoding the TIA-1 antigen may be prepared by standard methods using 2G9.4 (SEQ ID NO.:1) or T4T8.9-5 (SEQ ID NO.:2), or a portion thereof. Such a probe may be used in an assay employing, for example, PCR or in situ hybridization technology to indicate the presence of complementary nucleic acid in a given sample.

Deposits

The following deposits have been made with the American Type Culture Collection according to the requirements of the Budapest Treaty:

| Deposit | Date | Accession No. |
| --- | --- | --- |
| E. coli strain T4T8.9-5 | January 5, 1990 | 68202 |
| Hybridoma TIA-1 | January 5, 1990 | HB 10319 |

Applicants' assignee, The Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Other embodiments are within the following claims.

We claim:

1. Isolated DNA comprising a sequence encoding a polypeptide that is immunologically reactive with the monoclonal antibody produced by the hybridoma designated ATCC #HB 10319.

2. The isolated DNA of claim 1, wherein said DNA encodes a protein of approximately 40 kD.

3. The isolated DNA of claim 2, wherein said DNA comprises a nucleotide sequence substantially identical to SEQ ID NO:1.

4. The isolated DNA of claim 1, wherein said DNA encodes a protein of approximately 15 kD.

5. The isolated DNA of claim 3, wherein said polypeptide has an amino acid sequence substantially identical to that encoded by the plasmid designated ATCC number 68202.

6. The isolated DNA of claim 4, wherein said DNA comprises a nucleotide sequence substantially identical to SEQ ID NO:2.

7. A purified preparation of a vector, said vector comprising the isolated DNA of claim 1.

8. Isolated DNA which hybridizes under stringent conditions to a nucleic acid probe comprising a twenty-nucleotide segment of the coding sequence of the plasmid designated ATCC #68202.

9. A purified preparation of a vector, said vector comprising the isolated DNA of claim 7.

10. The isolated DNA of claim 8, wherein said probe comprises the entire coding sequence of the plasmid designated ATCC #68202.

11. Isolated DNA comprising a sequence encoding the polypeptide encoded by the plasmid designed ATCC number 68202.

12. The plasmid deposited as ATCC #68202.

13. A cell transformed with an isolated DNA comprising a sequence encoding a polypeptide that is immunologically reactive with the antibody produced by the hybridoma designated ATCC #HB 10319.

14. A method of producing a protein, said method comprising culturing the cell of claim 13 under conditions permitting expression of said isolated DNA, and recovering the protein encoded by said isolated DNA.

15. An essentially homogenous population of cells, each of which is transformed with an isolated DNA comprising a sequence encoding a polypeptide immunologically reactive with the antibody produced by the hybridoma designated ATCC #HB 10319.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2228
( B ) TYPE: nucleic acid
( C ) STRANDEDNESS: double
( D ) TOPOLOGY: linear ( x i ) SEQUENCE DESCRIPTION: SEQ ID NO:1:

```
GAGGTAGTGA AGGGCAGGGA GCTGGACCTG GAGGCGCCGC CGCGACAGCA GCAGCC                56

ATG GAG GAC GAG ATG CCC AAG ACT CTA TAC GTC GGT AAC CTT TCC AGA            104
Met Glu Asp Glu Met Pro Lys Thr Leu Tyr Val Gly Asn Leu Ser Arg
 1               5                  10                  15

GAT GTG ACA GAA GCT CTA ATT CTG CAA CTC TTT AGC CAG ATT GGA CCT            152
Asp Val Thr Glu Ala Leu Ile Leu Gln Leu Phe Ser Gln Ile Gly Pro
                20                  25                  30

TGT AAA AAC TGC AAA ATG ATT ATG GAT ACA GCT GGA AAT GAT CCC TAT            200
Cys Lys Asn Cys Lys Met Ile Met Asp Thr Ala Gly Asn Asp Pro Tyr
         35                  40                  45

TGT TTT GTG GAG TTT CAT GAG CAT CGT CAT GCA GCT GCA GCA TTA GCT            248
Cys Phe Val Glu Phe His Glu His Arg His Ala Ala Ala Ala Leu Ala
     50                  55                  60

GCT ATG AAT GGA CGG AAG ATA ATG GGT AAG GAA GTC AAA GTG AAT TGG            296
Ala Met Asn Gly Arg Lys Ile Met Gly Lys Glu Val Lys Val Asn Trp
 65                  70                  75                  80

GCA ACA ACC CCT AGC AGT CAA AAG AAA GAT ACA AGC AAT CAT TTC CAT            344
```

| | | | | | | | | | | | | | | | | |
|---|---|---|---|---|---|---|---|---|---|---|---|---|---|---|---|---|
| Ala | Thr | Thr | Pro | Ser<br>85 | Ser | Gln | Lys | Lys | Asp<br>90 | Thr | Ser | Asn | His | Phe<br>95 | His | |

| | | | | | | | | | | | | | | | | |
|---|---|---|---|---|---|---|---|---|---|---|---|---|---|---|---|---|
| GTC | TTT | GTT | GGT | GAT | CTC | AGC | CCA | GAA | ATT | ACA | ACT | GAA | GAT | ATA | AAA | 392 |
| Val | Phe | Val | Gly<br>100 | Asp | Leu | Ser | Pro | Glu<br>105 | Ile | Thr | Thr | Glu | Asp<br>110 | Ile | Lys | |
| GCT | GCT | TTT | GCA | CCA | TTT | GGA | AGA | ATA | TCA | GAT | GCC | CGA | GTG | GTA | AAA | 440 |
| Ala | Ala | Phe<br>115 | Ala | Pro | Phe | Gly | Arg<br>120 | Ile | Ser | Asp | Ala | Arg<br>125 | Val | Val | Lys | |
| GAC | ATG | GCA | ACA | GGA | AAG | TCT | AAG | GGA | TAT | GGC | TTT | GTC | TCC | TTT | TTC | 488 |
| Asp | Met<br>130 | Ala | Thr | Gly | Lys | Ser<br>135 | Lys | Gly | Tyr | Gly | Phe<br>140 | Val | Ser | Phe | Phe | |
| AAC | AAA | TGG | GAT | GCT | GAA | AAC | GCC | ATT | CAA | CAG | ATG | GGT | GGC | CAG | TGG | 536 |
| Asn<br>145 | Lys | Trp | Asp | Ala | Glu<br>150 | Asn | Ala | Ile | Gln | Gln<br>155 | Met | Gly | Gly | Gln | Trp<br>160 | |
| CTT | GGT | GGA | AGA | CAA | ATC | AGA | ACT | AAC | TGG | GCA | ACC | CGA | AAG | CCT | CCC | 584 |
| Leu | Gly | Gly | Arg | Gln<br>165 | Ile | Arg | Thr | Asn | Trp<br>170 | Ala | Thr | Arg | Lys | Pro<br>175 | Pro | |
| GCT | CCA | AAG | AGT | ACA | TAT | GAG | TCA | AAT | ACC | AAA | CAG | CTA | TCA | TAT | GAT | 632 |
| Ala | Pro | Lys | Ser<br>180 | Thr | Tyr | Glu | Ser | Asn<br>185 | Thr | Lys | Gln | Leu | Ser<br>190 | Tyr | Asp | |
| GAG | GTT | GTA | AAT | CAG | TCT | AGT | CCA | AGC | AAC | TGT | ACT | GTA | TAC | TGT | GGA | 680 |
| Glu | Val | Val<br>195 | Asn | Gln | Ser | Ser | Pro<br>200 | Ser | Asn | Cys | Thr | Val<br>205 | Tyr | Cys | Gly | |
| GGT | GTT | ACT | TCT | GGG | CTA | ACA | GAA | CAA | CTA | ATG | CGT | CAG | ACT | TTT | TCA | 728 |
| Gly | Val<br>210 | Thr | Ser | Gly | Leu | Thr<br>215 | Glu | Gln | Leu | Met | Arg<br>220 | Gln | Thr | Phe | Ser | |
| CCA | TTT | GGA | CAA | ATA | ATG | GAA | ATT | CGA | GTC | TTT | CCA | GAT | AAA | GGA | TAT | 776 |
| Pro<br>225 | Phe | Gly | Gln | Ile | Met<br>230 | Glu | Ile | Arg | Val | Phe<br>235 | Pro | Asp | Lys | Gly | Tyr<br>240 | |
| TCA | TTT | GTT | CGG | TTC | AAT | TCC | CAT | GAA | AGT | GCA | GCA | CAT | GCA | ATT | GTT | 824 |
| Ser | Phe | Val | Arg | Phe<br>245 | Asn | Ser | His | Glu | Ser<br>250 | Ala | Ala | His | Ala | Ile<br>255 | Val | |
| TCT | GTT | AAT | GGT | ACT | ACC | ATT | GAA | GGT | CAT | GTT | GTG | AAA | TGC | TAT | TGG | 872 |
| Ser | Val | Asn | Gly<br>260 | Thr | Thr | Ile | Glu | Gly<br>265 | His | Val | Val | Lys | Cys<br>270 | Tyr | Trp | |
| GGC | AAA | GAA | ACT | CTT | GAT | ATG | ATA | AAT | CCC | GTG | CAA | CAG | CAG | AAT | CAA | 920 |
| Gly | Lys | Glu | Thr<br>275 | Leu | Asp | Met | Ile | Asn<br>280 | Pro | Val | Gln | Gln | Gln<br>285 | Asn | Gln | |
| ATT | GGA | TAT | CCC | CAA | CCT | TAT | GGC | CAG | TGG | GGC | CAG | TGG | TAT | GGA | AAT | 968 |
| Ile | Gly<br>290 | Tyr | Pro | Gln | Pro | Tyr<br>295 | Gly | Gln | Trp | Gly | Gln<br>300 | Trp | Tyr | Gly | Asn | |
| GCA | CAA | CAA | ATT | GGC | CAG | TAT | ATG | CCT | AAT | GGT | TGG | CAA | GTT | CCT | GCA | 1016 |
| Ala<br>305 | Gln | Gln | Ile | Gly | Gln<br>310 | Tyr | Met | Pro | Asn | Gly<br>315 | Trp | Gln | Val | Pro | Ala<br>320 | |
| TAT | GGA | ATG | TAT | GGC | CAG | GCA | TGG | AAC | CAG | CAA | GGA | TTT | AAT | CAG | ACA | 1064 |
| Tyr | Gly | Met | Tyr | Gly<br>325 | Gln | Ala | Trp | Asn | Gln<br>330 | Gln | Gly | Phe | Asn | Gln<br>335 | Thr | |
| CAG | TCT | TCT | GCA | CCA | TGG | ATG | GGA | CCA | AAT | TAT | GGA | GTG | CAA | CCG | CCT | 1112 |
| Gln | Ser | Ser | Ala<br>340 | Pro | Trp | Met | Gly | Pro<br>345 | Asn | Tyr | Gly | Val | Gln<br>350 | Pro | Pro | |
| CAA | GGG | CAA | AAT | GGC | AGC | ATG | TTG | CCC | AAT | CAG | CCT | TCT | GGG | TAT | CGA | 1160 |
| Gln | Gly | Gln | Asn | Gly<br>355 | Ser | Met | Leu | Pro | Asn<br>360 | Gln | Pro | Ser | Gly<br>365 | Tyr | Arg | |
| GTG | GCA | GGG | TAT | GAA | ACC | CAG | TGAATAAGGA | CTCCAGAATC | TAAAGCCAGT | | | | | | | 1211 |
| Val | Ala | Gly<br>370 | Tyr | Glu | Thr | Gln<br>375 | | | | | | | | | | |

```
GGCTTGAGGC TACAGGGAGT GTAGTAAAGC CGTTGTTTAC TTAAAGATTT ATCAAATCAG 1271
TCAGTGCAAA TGTCAGATAC AATGTATTTA TTTAAAAGAT TCATTTTTAA TCATGAAATT 1331
ACTTATCATC CACATTGTTT TAAAAAGAAA CAAGATGCTG GATGTCTGCC AATTTTTGCC 1391
TTCATTACCT TTTTTGATAA AGTTTCTCAG ATCCTTGTTT CAAACACAAA TGCAGGGATT 1451
```

-continued

```
GCTGCCACTT TTTAACTATT AAGAGGCAGA AAATTGCACA ATATTGAACT TTTTTCCACT  1511

GAAGTAGTGT GCAGTTCTAG TTTGCATTCC TGATATGATT TAAAACATGT AATATAAAGA  1571

TGTTAAAAAA AAAAACCAAA ACTGTGCAGA GTCTAGAAGT TGTTTGTCAT CTTCAGCTTG  1631

TGCACAATTC TGTTTTAGGT TAAAAAAAGG CATTGTTTGA GCTGTCCCAT CTCCACTGTT  1691

ATCCCTTTGG GTTTTTAAT ATAAATTATT AGTTTACATC ATTTTTGTAT CTACATCTTT  1751

TTTCACAAAT TTGTCTTGCC TTATTAAAGT TCTGTAAAAT ATACTTAAAT GGAAAAAATG  1811

ATGTTCATTT AGATTGAAAA CTTTTCTCAG ATGGATTGAT AATTGCATTC ATCTTGTGTT  1871

TTATATGAGA AGGTGCCTCA AGAATTTCCT GTTGGATTTG TTTAAAAGGA TTTTTATCTT  1931

TCGTGATAAA CTTTGCTGTG TACCAGGAAC TATAAAAACA AAAACTTGTT ACTAAAGAAA  1991

ATATCTGAAA TGTGATAAGT TCTTATGCCA TGTTAATTTC ATGTGTCAAC TTCAACATTT  2051

ACATGTATTA TTTCATTATG TAAAATGTTT TAGCAATTTA ATATTTTGCA CAGTTAGCAA  2111

ACTTTGTATG TCATTTCCTT CAAGGCATCA TGCAGAGTTG ACATGAGATT TATAAGGTTT  2171

TAAGTTGTTT GCATGTGAAA ATCAAATACA TACTTTGGTA GTCTTTGAAA AAAAAA      2228
```

(2) INFORMATION FOR SEQ ID NO:2:

(i) SEQUENCE CHARACTERISTICS:
        (A) LENGTH: 1618
        (B) TYPE: nucleic acid
        (C) STRANDEDNESS: double
        (D) TOPOLOGY: linear (xi) SEQUENCE DESCRIPTION: SEQ ID NO:2:

```
TACCAAACAG CTATCATATG ATGAGGTTGT AAATCAGTCT AGTCCAAGCA ACTGTACTGT   60

ATACTGTGGA GGTGTTACTT CTGGGCTAAC AGAACAACTA ATGCGTCAGA CTTTTTCACC  120

ATTTGGACAA ATA ATG GAA ATT CGA GTC TTT CCA GAT AAA GGA TAT TCA    169
            Met Glu Ile Arg Val Phe Pro Asp Lys Gly Tyr Ser
              1               5                  10

TTT GTT CGG TTC AAT TCC CAT GAA AGT GCA GCA CAT GCA ATT GTT TCT   217
Phe Val Arg Phe Asn Ser His Glu Ser Ala Ala His Ala Ile Val Ser
         15              20                  25

GTT AAT GGT ACT ACC ATT GAA GGT CAT GTT GTG AAA TGC TAT TGG GGC   265
Val Asn Gly Thr Thr Ile Glu Gly His Val Val Lys Cys Tyr Trp Gly
     30              35                  40

AAA GAA ACT CTT GAT ATG ATA AAT CCC GTG CAA CAG CAG AAT CAA ATT   313
Lys Glu Thr Leu Asp Met Ile Asn Pro Val Gln Gln Gln Asn Gln Ile
 45              50                  55                  60

GGA TAT CCC CAA CCT TAT GGC CAG TGG GGC CAG TGG TAT GGA AAT GCA   361
Gly Tyr Pro Gln Pro Tyr Gly Gln Trp Gly Gln Trp Tyr Gly Asn Ala
             65                  70                  75

CAA CAA ATT GGC CAG TAT ATG CCT AAT GGT TGG CAA GTT CCT GCA TAT   409
Gln Gln Ile Gly Gln Tyr Met Pro Asn Gly Trp Gln Val Pro Ala Tyr
         80                  85                  90

GGA ATG TAT GGC CAG GCA TGG AAC CAG CAA GGA TTT AAT CAG ACA CAG   457
Gly Met Tyr Gly Gln Ala Trp Asn Gln Gln Gly Phe Asn Gln Thr Gln
     95                 100                 105

TCT TCT GCA CCA TGG ATG GGA CCA AAT TAT GGA GTG CAA CCG CCT CAA   505
Ser Ser Ala Pro Trp Met Gly Pro Asn Tyr Gly Val Gln Pro Pro Gln
110                 115                 120

GGG CAA AAT GGC AGC ATG TTG CCC AAT CAG CCT TCT GGG TAT CGA GTG   553
Gly Gln Asn Gly Ser Met Leu Pro Asn Gln Pro Ser Gly Tyr Arg Val
125                 130                 135                 140

GCA GGG TAT GAA ACC CAG TGAATAAGGA CTCCAGAATC TAAAGCCAGT          601
Ala Gly Tyr Glu Thr Gln
             145
```

```
GGCTTGAGGC TACAGGGAGT GTAGTAAAGC CGTTGTTTAC TTAAAGATTT ATCAAATCAG    661
TCAGTGCAAA TGTCAGATAC AATGTATTTA TTTAAAAGAT TCATTTTTAA TCATGAAATT    721
ACTTATCATC CACATTGTTT TAAAAAGAAA CAAGATGCTG GATGTCTGCC AATTTTTGCC    781
TTCATTACCT TTTTTGATAA AGTTCTCAG  ATCCTTGTTT CAAACACAAA TGCAGGGATT    841
GCTGCCACTT TTTAACTATT AAGAGGCAGA AAATTGCACA ATATTGAACT TTTTTCCACT    901
GAAGTAGTGT GCAGTTCTAG TTTGCATTCC TGATATGATT TAAAACATGT AATATAAAGA    961
TGTTAAAAAA AAAAACCAAA ACTGTGCAGA GTCTAGAAGT TGTTTGTCAT CTTCAGCTTG   1021
TGCACAATTC TGTTTTAGGT TAAAAAAAGG CATTGTTTGA GCTGTCCCAT CTCCACTGTT   1081
ATCCCTTTGG GTTTTTTAAT ATAAATTATT AGTTACATC  ATTTTTGTAT CTACATCTTT   1141
TTTCACAAAT TTGTCTTGCC TTATTAAAGT TCTGTAAAAT ATACTTAAAT GGAAAAAATG   1201
ATGTTCATTT AGATTGAAAA CTTTTCTCAG ATGGATTGAT AATTGCATTC ATCTTGTGTT   1261
TTATATGAGA AGGTGCCTCA AGAATTTCCT GTTGGATTTG TTTAAAAGGA TTTTTATCTT   1321
TCGTGATAAA CTTTGCTGTG TACCAGGAAC TATAAAAACA AAACTTGTT  ACTAAAGAAA   1381
ATATCTGAAA TGTGATAAGT TCTTATGCCA TGTTAATTTC ATGTGTCAAC TTCAACATTT   1441
ACATGTATTA TTTCATTATG TAAAATGTTT TAGCAATTTA ATATTTTGCA CAGTTAGCAA   1501
ACTTTGTATG TCATTTCCTT CAAGGCATCA TGCAGAGTTG ACATGAGATT TATAAGGTTT   1561
TAAGTTGTTT GCATGTGAAA ATCAAATACA TACTTTGGTA GTCTTTGAAA AAAAAA      1618
```